(12) United States Patent
Luche et al.

(10) Patent No.: US 7,029,898 B2
(45) Date of Patent: Apr. 18, 2006

(54) DSP-11 DUAL-SPECIFICITY PHOSPHATASE

(75) Inventors: Ralf M. Luche, Seattle, WA (US); Bo Wei, Kirkland, WA (US)

(73) Assignee: CEPTYR, Inc., Bothell, WA (US)

( * ) Notice: Subject to any disclaimer, the term of this patent is extended or adjusted under 35 U.S.C. 154(b) by 0 days.

(21) Appl. No.: 10/655,073

(22) Filed: Sep. 4, 2003

(65) Prior Publication Data

US 2004/0043411 A1 Mar. 4, 2004

Related U.S. Application Data

(63) Continuation of application No. 09/619,380, filed on Jul. 19, 2000, now Pat. No. 6,649,391
(60) Provisional application No. 60/144,557, filed on Jul. 20, 1999.

(51) Int. Cl.
| | |
|---|---|
| *C12N 9/16* | (2006.01) |
| *C12N 1/20* | (2006.01) |
| *C12N 15/00* | (2006.01) |
| *C07H 21/04* | (2006.01) |
| *A61K 38/00* | (2006.01) |

(52) U.S. Cl. ................. 435/196; 435/252.3; 435/320.1; 536/23.2; 530/300; 530/350
(58) Field of Classification Search ................. 435/196, 435/252.3, 320.1; 536/23.2; 530/300, 350
See application file for complete search history.

(56) References Cited

FOREIGN PATENT DOCUMENTS

| WO | WO 95/21923 | 8/1995 |
|---|---|---|
| WO | WO 97/00315 | 1/1997 |
| WO | WO 97/06245 | 2/1997 |
| WO | WO 98/04712 | 2/1998 |

OTHER PUBLICATIONS

Adams and Cory, "The Bcl–2 Protein Family: Arbiters of Cell Survival," *Science* 281(5381):1322–1326, 1998.
Alessi et al., "The Human CL100 Gene Encodes a Tyr/Thr –Protein Phosphatase Which Potently and Specifically Inactivates MAP Kinase and Suppresses Its Activation by Oncogenic Ras in Xenopus Oocyte Extracts," *Oncogene* 8(7):2015–2020, 1993.
Ashkenazi and Dixit, "Death Receptors: Signaling and Modulation," *Science* 281(5381), 1305–1308, 1998.
Evan and Littlewood, "A Matter of Life and Cell Death," *Science* 281(5381):1317–1322, 1998.
Fauman and Saper, "Structure and Function of the Protein Tyrosine Phosphatases," *TiBS* 21(11):413–417, 1996.
Groom et al., "Differential Regulation of the MAP, SAP and RK/p38 Kinases by Pyst1, a Novel Cytosolic Dual–Specificity Phosphatase," *The EMBO J.* 15(14):3621–3632, 1996.
Guan and Butch, "Isolation and Characterization of a Novel Dual Specific Phosphatase, HVH2, Which Selectively Dephosphorylates the Mitogen–Activated Protein Kinase," *The J. of Biological Chemistry* 270(13):7197–7203, 1995.
Jia, "Protein Phosphatases: Structures and Implications," *Biochimie et Biologie Cellulaire* 75(1):17–26, 1997.
Keyse, "An Emerging Family of Dual Specificity MAP Kinase Phosphatases," *Biochimica et Biophysica Acta* 1265:152–160, 1995.
Keyse and Emslie, "Oxidative Stress and Heat Shock Induce a Human Gene Encoding a Protein–Tyrosine Phosphatase," *Nature* 359:644–647, 1992.
Thornberry and Lazebnik, "Caspases: Enemies Within," *Science* 281(5381):1312–1316, 1998.
Walton and Dixon, "Protein Tyrosine Phosphatases," *Annu. Rev. Biochem.* 62:101–120, 1993.
Ward et al., "Control of MAP Kinase Activation by the Mitogen–Induced Threonine/Tyrosine Phosphatase PAC1," *Nature* 367(6464):651–654, 1994.
Zheng and Guan, "Dephosphorylation and Inactivation of the Mitogen–Activated Protein Kinase by a Mitogen–Induced Thr/Tyr Protein Phosphatase," *The J. of Biological Chemistry* 268(22):16116–16119, 1993.
GenBank Acc. No. AF086553.
GenBank Acc. No. AA479435, Jun. 19, 1997.
GenBank Acc. No. AC004099, Jun. 6, 2000.
GenBank Acc. No. AK000449, Jun. 22, 2000.
Flint, A J. et al., "Development of "substrate–trapping" mutants to identify physiological substrates of protein tyrosine phosphatases," *Proc. Natl. Acad. Sci.*, USA, 94:1680–1685, Mar. 1997.
Muda, M. et al., "Molecular Cloning and Functional Characterization of a Novel Mitogen–activated Protein Kinase Phosphatase, MKP–4," *The Journal of Biological Chemistry*, 272(8):5141–5151, Feb. 21, 1997.

*Primary Examiner*—Tekchand Saidha
(74) *Attorney, Agent, or Firm*—Seed IP Law Group

(57) ABSTRACT

Compositions and methods are provided for the treatment of conditions associated with cell proliferation, cell differentiation and cell survival. In particular, the dual-specificity phosphatase DSP-11, and polypeptide variants thereof that stimulate dephosphorylation of DSP-11 substrates, are provided. The polypeptides may be used, for example, to identify antibodies and other agents that inhibit DSP-11 activity. The polypeptides and agents may be used to modulate cell proliferation, differentiation and survival.

5 Claims, 4 Drawing Sheets

DSP-11, 450 base pairs

TGACCCGCTG TCCTGTGCCC TTTCCCAGCG ATGGGCGTGC AGCCCCCCAA CTTCTCCTGG GTGCTTCCGG GCCGGCTGGC GGGACTGGCG
CTGCCGCGGC TCCCCGCCCA CTACCAGTTC CTGTTGGACC TGGGCGTGCG GCACCTGGTG TCCCTGACGG AGCGCGGGCC CCCTCACAGC
GACAGCTGCC CCGGCCTCAC CCTGCACCGC CTGCGCATCC CCGACTTCTG CCCGCCGGCC CCCGACCAGA TCGACCGCTT CGTGCAGATC
GTGGACGAGG CCAACGCACG GGAGAGGCT GTGGGAGTGC ACTGTGCTCT GGGCTTTGGC CGCACTGGCA CCATGCTGGC CTGTTACCTG
GTGAAGGAGC GGGGCTTGGC TGCAGGAGAT GCCATTGCTG AAATCCGACG ACTACGACCC GGCTCCATCG AGACCTATGA GCAGGAGAAA
GCAGTCTTCC AGTTCTACCA GCGAACGAAA TAAGGGGCCT TAGTACCCTT CTACCAGGCC CTCACTCCCC TTCCCCATGT TGTCGATGGG
GCCAGAGATG AAGGGAAGTG GACTAAAGTA TTAAACCCTC TAGCTCCCAT TGGCTGAAGA CACTGAAGTA GCCCACCCCT GCAGGCAGGT
CCTGATTGAA GGGGAGGCTT GTACTGCTTT GTTGAATAAA TGAGTTTTAC GAACCAAAAA AAAAAAAAAA AAAAAAA

Fig. 1

DSP-11, 150 amino acids

MGVQPPNFSWVLPGRLAGLALPRLPAHYQFLLDLGVRHLVSLTERGPPHSDSCPGLTLHRLRIPDFCPPAPDQIDRFVQIVDEANARGEAVGVHCALG
FGRTGTMLACYLVKERGLAAGDAIAEIRRLRPGSIETYEQEKAVFQFYQRTK

>murine DSP-11 variant coding sequence atgggcgtgcaaccccccaacttctcctgggtgcttccgggacggctggccggactggc
gttgccccggctgcccgcgcactaccagttcctgctggaccagggtgtgcggcacctgg
tgtccctgacggagcgcggaccccctcacagtgacagctgtcccggcctcacgctgcac
cgaatgcgcatccctgactttgcccgccgtccccggaacagatcgaccaatttgtgaa
gatcgtggacgaggccaatgcccggggagaggctgttggagtgcactgtgccctaggct
ttggccgcactggcaccatgctagcctgctacttggtgaaggagcgggctttggcgcCa
ggagatgccattgctgagatccggcgcctgcgaccaggatccattgagacgtatgaaca
ggagaaggccgtcttccagttctaccagcgaacaaaatga

*Fig. 5*

>murine DSP-11 variant amino acid sequence

MGVQPPNFSWVLPGRLAGLALPRLPAHYQFLLDQGVRHLVSLTERGPPHSDSCPGLTLH
RMRIPDFCPPSPEQIDQFVKIVDEANARGEAVGVHCALGFGRTGTMLACYLVKERALAP
GDAIAEIRRLRPGSIETYEQEKAVFQFYQRTK*

*Fig. 6*

SEQUENCE LISTING

<160> NUMBER OF SEQ IDS NOS: 22

<210> SEQ ID NO 1
<211> LENGTH: 707
<212> TYPE: DNA
<213> ORGANISM: Homo sapiens

<400> SEQUENCE: 1

```
tgacccgctg tcctgtgccc tttcccagcg atgggcgtgc agccccccaa cttctcctgg      60
gtgcttccgg gccggctggc gggactggcg ctgccgcggc tccccgccca ctaccagttc     120
ctgttggacc tgggcgtgcg gcacctggtg tccctgacgg agcgcgggcc ccctcacagc     180
gacagctgcc ccggcctcac cctgcaccgc ctgcgcatcc ccgacttctg cccgccggcc     240
cccgaccaga tcgaccgctt cgtgcagatc gtggacgagg ccaacgcacg gggagaggct     300
gtgggagtgc actgtgctct gggctttggc cgcactggca ccatgctggc ctgttacctg     360
gtgaaggagc ggggcttggc tgcaggagat gccattgctg aaatccgacg actacgaccc     420
ggctccatcg agacctatga gcaggagaaa gcagtcttcc agttctacca gcgaacgaaa     480
taagggcct tagtacccttt ctaccaggcc ctcactcccc ttccccatgt tgtcgatggg     540
gccagagatg aagggaagtg gactaaagta ttaaaccctc tagctcccat ggctgaaga      600
cactgaagta gcccacccct gcaggcaggt cctgattgaa ggggaggctt gtactgcttt     660
gttgaataaa tgagttttac gaaccaaaaa aaaaaaaaaa aaaaaaa                   707
```

<210> SEQ ID NO 2
<211> LENGTH: 150
<212> TYPE: PRT
<213> ORGANISM: Homo sapiens

<400> SEQUENCE: 2

```
Met Gly Val Gln Pro Pro Asn Phe Ser Trp Val Leu Pro Gly Arg Leu
  1               5                  10                  15

Ala Gly Leu Ala Leu Pro Arg Leu Pro Ala His Tyr Gln Phe Leu Leu
             20                  25                  30

Asp Leu Gly Val Arg His Leu Val Ser Leu Thr Glu Arg Gly Pro Pro
         35                  40                  45

His Ser Asp Ser Cys Pro Gly Leu Thr Leu His Arg Leu Arg Ile Pro
     50                  55                  60

Asp Phe Cys Pro Pro Ala Pro Asp Gln Ile Asp Arg Phe Val Gln Ile
 65                  70                  75                  80

Val Asp Glu Ala Asn Ala Arg Gly Glu Ala Val Gly Val His Cys Ala
                 85                  90                  95

Leu Gly Phe Gly Arg Thr Gly Thr Met Leu Ala Cys Tyr Leu Val Lys
            100                 105                 110

Glu Arg Gly Leu Ala Ala Gly Asp Ala Ile Ala Glu Ile Arg Arg Leu
        115                 120                 125

Arg Pro Gly Ser Ile Glu Thr Tyr Glu Gln Glu Lys Ala Val Phe Gln
    130                 135                 140

Phe Tyr Gln Arg Thr Lys
145                 150
```

<210> SEQ ID NO 3
<211> LENGTH: 21
<212> TYPE: PRT
<213> ORGANISM: Homo sapiens

```
<400> SEQUENCE: 3

Val Gly Val His Cys Ala Leu Gly Phe Gly Arg Thr Gly Thr Met Leu
1               5                   10                  15

Ala Cys Tyr Leu Val
            20

<210> SEQ ID NO 4
<211> LENGTH: 24
<212> TYPE: PRT
<213> ORGANISM: Homo sapiens

<400> SEQUENCE: 4

Asn Gly Arg Val Leu Val His Cys Gln Ala Gly Ile Ser Arg Ser Gly
1               5                   10                  15

Thr Asn Ile Leu Ala Tyr Leu Met
            20

<210> SEQ ID NO 5
<211> LENGTH: 27
<212> TYPE: DNA
<213> ORGANISM: Artificial Sequence
<220> FEATURE:
<223> OTHER INFORMATION: PCR primer

<400> SEQUENCE: 5
cgggtcgtag tcgtcggatt tcagcaa                                27

<210> SEQ ID NO 6
<211> LENGTH: 24
<212> TYPE: DNA
<213> ORGANISM: Artificial Sequence
<220> FEATURE:
<223> OTHER INFORMATION: PCR primer

<400> SEQUENCE: 6
cctctccccg tgcgttggcc tcgt                                   24

<210> SEQ ID NO 7
<211> LENGTH: 18
<212> TYPE: DNA
<213> ORGANISM: Artificial Sequence
<220> FEATURE:
<223> OTHER INFORMATION: PCR primer

<400> SEQUENCE: 7
cgcacgggga gaggctgt                                          18

<210> SEQ ID NO 8
<211> LENGTH: 41
<212> TYPE: DNA
<213> ORGANISM: Artificial Sequence
<220> FEATURE:
<223> OTHER INFORMATION: PCR primer

<400> SEQUENCE: 8
gaggaataat aaatgacccg ctgtcctgtg ccctttccca g                41

<210> SEQ ID NO 9
<211> LENGTH: 34
<212> TYPE: DNA
<213> ORGANISM: Artificial Sequence
<220> FEATURE:
<223> OTHER INFORMATION: PCR primer
```

-continued

<400> SEQUENCE: 9
tttcgttcgc tggtagaact ggaagactgc tttc                                34

<210> SEQ ID NO 10
<211> LENGTH: 27
<212> TYPE: DNA
<213> ORGANISM: Artificial Sequence
<220> FEATURE:
<223> OTHER INFORMATION: PCR primer

<400> SEQUENCE: 10
atgggcgtgc aacccccaa cttctcc                                         27

<210> SEQ ID NO 11
<211> LENGTH: 34
<212> TYPE: DNA
<213> ORGANISM: Artificial Sequence
<220> FEATURE:
<223> OTHER INFORMATION: PCR primer

<400> SEQUENCE: 11 tcatttgtt cgctggtaga actggaagac ggcc                                 34

<210> SEQ ID NO 12
<211> LENGTH: 453
<212> TYPE: DNA
<213> ORGANISM: Mus musculus

<400> SEQUENCE: 12
atgggcgtgc aacccccaa cttctcctgg gtgcttccgg gacggctggc cggactggcg     60
ttgccccggc tgcccgcgca ctaccagttc ctgctggacc agggtgtgcg gcacctggtg   120
tccctgacgg agcgcggacc ccctcacagt gacagctgtc ccggcctcac gctgcaccga   180
atgcgcatcc ctgacttttg cccgccgtcc ccggaacaga tcgaccaatt tgtgaagatc   240
gtggacgagg ccaatgcccg gggagaggct gttggagtgc actgtgccct aggctttggc   300
cgcactggca ccatgctagc ctgctacttg gtgaaggagc gggctttggc gccaggagat   360
gccattgctg agatccggcg cctgcgacca ggatccattg agacgtatga acaggagaag   420
gccgtcttcc agttctacca gcgaacaaaa tga                                453

<210> SEQ ID NO 13
<211> LENGTH: 150
<212> TYPE: PRT
<213> ORGANISM: Mus musculus

<400> SEQUENCE: 13

Met Gly Val Gln Pro Pro Asn Phe Ser Trp Val Leu Pro Gly Arg Leu
 1               5                   10                  15

Ala Gly Leu Ala Leu Pro Arg Leu Pro Ala His Tyr Gln Phe Leu Leu
                20                  25                  30

Asp Gln Gly Val Arg His Leu Val Ser Leu Thr Glu Arg Gly Pro Pro
            35                  40                  45

His Ser Asp Ser Cys Pro Gly Leu Thr Leu His Arg Met Arg Ile Pro
        50                  55                  60

Asp Phe Cys Pro Pro Ser Pro Glu Gln Ile Asp Gln Phe Val Lys Ile
65                  70                  75                  80

Val Asp Glu Ala Asn Ala Arg Gly Glu Ala Val Gly Val His Cys Ala
                85                  90                  95

Leu Gly Phe Gly Arg Thr Gly Thr Met Leu Ala Cys Tyr Leu Val Lys
                100                 105                 110

```
Glu Arg Ala Leu Ala Pro Gly Asp Ala Ile Ala Glu Ile Arg Arg Leu
        115                 120                 125

Arg Pro Gly Ser Ile Glu Thr Tyr Glu Gln Glu Lys Ala Val Phe Gln
    130                 135                 140

Phe Tyr Gln Arg Thr Lys
145                 150

<210> SEQ ID NO 14
<211> LENGTH: 170
<212> TYPE: PRT
<213> ORGANISM: Homo sapiens

<400> SEQUENCE: 14

Ser Asp Leu Asp Arg Asp Pro Asn Ser Ala Thr Asp Ser Asp Gly Ser
1               5                   10                  15

Pro Leu Ser Asn Ser Gln Pro Ser Phe Pro Val Glu Ile Leu Pro Phe
            20                  25                  30

Leu Tyr Leu Gly Cys Ala Lys Asp Ser Thr Asn Leu Asp Val Leu Glu
        35                  40                  45

Glu Phe Gly Ile Lys Tyr Ile Leu Asn Val Thr Pro Asn Leu Pro Asn
    50                  55                  60

Leu Phe Glu Asn Ala Gly Glu Phe Lys Tyr Lys Gln Ile Pro Ile Ser
65                  70                  75                  80

Asp His Trp Ser Gln Asn Leu Ser Gln Phe Phe Pro Glu Ala Ile Ser
                85                  90                  95

Phe Ile Asp Glu Ala Arg Gly Lys Asn Cys Gly Val Leu Val His Cys
            100                 105                 110

Leu Ala Gly Ile Ser Arg Ser Val Thr Val Thr Val Ala Tyr Leu Met
        115                 120                 125

Gln Lys Leu Asn Leu Ser Met Asn Asp Ala Tyr Asp Ile Val Lys Met
    130                 135                 140

Lys Lys Ser Asn Ile Ser Pro Asn Phe Asn Phe Met Gly Gln Leu Leu
145                 150                 155                 160

Asp Phe Glu Arg Thr Leu Gly Leu Ser Ser
                165                 170

<210> SEQ ID NO 15
<211> LENGTH: 168
<212> TYPE: PRT
<213> ORGANISM: Homo sapiens

<400> SEQUENCE: 15

Asp Arg Glu Leu Pro Ser Ser Ala Thr Glu Ser Asp Gly Ser Pro Val
1               5                   10                  15

Pro Ser Ser Gln Pro Ala Phe Pro Val Gln Ile Leu Pro Tyr Leu Tyr
            20                  25                  30

Leu Gly Cys Ala Lys Asp Ser Thr Asn Leu Asp Val Leu Gly Lys Tyr
        35                  40                  45

Gly Ile Lys Tyr Ile Leu Asn Val Thr Pro Asn Leu Pro Asn Ala Phe
    50                  55                  60

Glu His Gly Gly Glu Phe Thr Tyr Lys Gln Ile Pro Ile Ser Asp His
65                  70                  75                  80

Trp Ser Gln Asn Leu Ser Gln Phe Phe Pro Glu Ala Ile Ser Phe Ile
                85                  90                  95

Asp Glu Ala Arg Ser Lys Lys Cys Gly Val Leu Val His Cys Leu Ala
            100                 105                 110
```

```
Gly Ile Ser Arg Ser Val Thr Val Thr Val Ala Tyr Leu Met Gln Lys
            115                 120                 125

Met Asn Leu Ser Leu Asn Asp Ala Tyr Asp Phe Val Lys Arg Lys Lys
130                 135                 140

Ser Asn Ile Ser Pro Asn Phe Asn Phe Met Gly Gln Leu Leu Asp Phe
145                 150                 155                 160

Glu Arg Thr Leu Gly Leu Ser Ser
                165
```

<210> SEQ ID NO 16
<211> LENGTH: 170
<212> TYPE: PRT
<213> ORGANISM: Homo sapiens

<400> SEQUENCE: 16

```
Gly Leu Cys Glu Gly Lys Pro Ala Ala Leu Pro Met Ser Leu Ser
1               5                   10                  15

Gln Pro Cys Leu Pro Val Pro Ser Val Gly Leu Thr Arg Ile Leu Pro
                20                  25                  30

His Leu Tyr Leu Gly Ser Gln Lys Asp Val Leu Asn Lys Asp Leu Met
            35                  40                  45

Thr Gln Asn Gly Ile Ser Tyr Val Leu Asn Ala Ser Asn Ser Cys Pro
50                  55                  60

Lys Pro Asp Phe Ile Cys Glu Ser Arg Phe Met Arg Val Pro Ile Asn
65                  70                  75                  80

Asp Asn Tyr Cys Glu Lys Leu Leu Pro Trp Leu Asp Lys Ser Ile Glu
                85                  90                  95

Phe Ile Asp Lys Ala Lys Leu Ser Ser Cys Gln Val Ile Val His Cys
                100                 105                 110

Leu Ala Gly Ile Ser Arg Ser Ala Thr Ile Ala Ile Ala Tyr Ile Met
            115                 120                 125

Lys Thr Met Gly Met Ser Ser Asp Asp Ala Tyr Arg Phe Val Lys Asp
130                 135                 140

Arg Arg Pro Ser Ile Ser Pro Asn Phe Asn Phe Leu Gly Gln Leu Leu
145                 150                 155                 160

Glu Tyr Glu Arg Thr Leu Lys Leu Leu Ala
                165                 170
```

<210> SEQ ID NO 17
<211> LENGTH: 168
<212> TYPE: PRT
<213> ORGANISM: Homo sapiens

<400> SEQUENCE: 17

```
Pro Ala Gln Ala Leu Pro Pro Ala Gly Ala Glu Asn Ser Asn Ser Asp
1               5                   10                  15

Pro Arg Val Pro Ile Tyr Asp Gln Gly Gly Pro Val Glu Ile Leu Pro
                20                  25                  30

Tyr Leu Tyr Leu Gly Ser Cys Asn His Ser Ser Asp Leu Gln Gly Leu
            35                  40                  45

Gln Ala Cys Gly Ile Thr Ala Val Leu Asn Val Ser Ala Ser Cys Pro
50                  55                  60

Asn His Phe Glu Gly Leu Phe His Tyr Lys Ser Ile Pro Val Glu Asp
65                  70                  75                  80

Asn Gln Met Val Glu Ile Ser Ala Trp Phe Gln Glu Ala Ile Ser Phe
                85                  90                  95
```

-continued

Ile Asp Ser Val Lys Asn Ser Gly Gly Arg Val Leu Val His Cys Gln
            100                 105                 110

Ala Gly Ile Ser Arg Ser Ala Thr Ile Cys Leu Ala Tyr Leu Ile Gln
        115                 120                 125

Ser His Arg Val Arg Leu Asp Glu Ala Phe Asp Phe Val Lys Gln Arg
    130                 135                 140

Arg Gly Val Ile Ser Pro Asn Phe Ser Phe Met Gly Gln Leu Leu Gln
145                 150                 155                 160

Leu Glu Thr Gln Val Leu Cys His
                165

<210> SEQ ID NO 18
<211> LENGTH: 169
<212> TYPE: PRT
<213> ORGANISM: Homo sapiens

<400> SEQUENCE: 18

Pro Leu Ser Thr Ser Val Pro Asp Ser Ala Glu Ser Gly Cys Ser Ser
1               5                   10                  15

Cys Ser Thr Pro Leu Tyr Asp Gln Gly Gly Pro Val Glu Ile Leu Pro
            20                  25                  30

Phe Leu Tyr Leu Gly Ser Ala Tyr His Ala Ser Arg Lys Asp Met Leu
        35                  40                  45

Asp Ala Leu Gly Ile Thr Ala Leu Ile Asn Val Ser Ala Asn Cys Pro
    50                  55                  60

Asn His Phe Glu Gly His Tyr Gln Tyr Lys Ser Ile Pro Val Glu Asp
65                  70                  75                  80

Asn His Lys Ala Asp Ile Ser Ser Trp Phe Asn Glu Ala Ile Asp Phe
                85                  90                  95

Ile Asp Ser Ile Lys Asn Ala Gly Gly Arg Val Phe Val His Cys Gln
            100                 105                 110

Ala Gly Ile Ser Arg Ser Ala Thr Ile Cys Leu Ala Tyr Leu Met Arg
        115                 120                 125

Thr Asn Arg Val Lys Leu Asp Glu Ala Phe Glu Phe Val Lys Gln Arg
    130                 135                 140

Arg Ser Ile Ile Ser Pro Asn Phe Ser Phe Met Gly Gln Leu Leu Gln
145                 150                 155                 160

Phe Glu Ser Gln Val Leu Ala Pro His
                165

<210> SEQ ID NO 19
<211> LENGTH: 169
<212> TYPE: PRT
<213> ORGANISM: Homo sapiens

<400> SEQUENCE: 19

Pro Val Pro Pro Ser Ala Thr Glu Pro Leu Asp Leu Gly Cys Ser Ser
1               5                   10                  15

Cys Gly Thr Pro Leu His Asp Gln Gly Gly Pro Val Glu Ile Leu Pro
            20                  25                  30

Phe Leu Tyr Leu Gly Ser Ala Tyr His Ala Ala Arg Arg Asp Met Leu
        35                  40                  45

Asp Ala Leu Gly Ile Thr Ala Leu Leu Asn Val Ser Ser Asp Cys Pro
    50                  55                  60

Asn His Phe Glu Gly His Tyr Gln Tyr Lys Cys Ile Pro Val Glu Asp
65                  70                  75                  80

```
Asn His Lys Ala Asp Ile Ser Ser Trp Phe Met Glu Ala Ile Glu Tyr
                85                  90                  95

Ile Asp Ala Val Lys Asp Cys Arg Gly Arg Val Leu Val His Cys Gln
                100                 105                 110

Ala Gly Ile Ser Arg Ser Ala Thr Ile Cys Leu Ala Tyr Leu Met Met
                115                 120                 125

Lys Lys Arg Val Arg Leu Glu Glu Ala Phe Glu Phe Val Lys Gln Arg
            130                 135                 140

Arg Ser Ile Ile Ser Pro Asn Phe Ser Phe Met Gly Gln Leu Leu Gln
145                 150                 155                 160

Phe Glu Ser Gln Val Leu Ala Thr Ser
                165
```

<210> SEQ ID NO 20
<211> LENGTH: 171
<212> TYPE: PRT
<213> ORGANISM: Homo sapiens

<400> SEQUENCE: 20

```
Ser Glu Arg Ala Leu Ile Ser Gln Cys Gly Lys Pro Val Val Asn Val
1               5                   10                  15

Ser Tyr Arg Pro Ala Tyr Asp Gln Gly Gly Pro Val Glu Ile Leu Pro
                20                  25                  30

Phe Leu Tyr Leu Gly Ser Ala Tyr His Ala Ser Lys Cys Glu Phe Leu
            35                  40                  45

Ala Asn Leu His Ile Thr Ala Leu Leu Asn Val Ser Arg Arg Thr Ser
50                  55                  60

Glu Ala Cys Met Thr His Leu His Tyr Lys Trp Ile Pro Val Glu Asp
65                  70                  75                  80

Ser His Thr Ala Asp Ile Ser Ser His Phe Gln Glu Ala Ile Asp Phe
                85                  90                  95

Ile Asp Cys Val Arg Glu Lys Gly Gly Lys Val Leu Val His Cys Glu
                100                 105                 110

Ala Gly Ile Ser Arg Ser Pro Thr Ile Cys Met Ala Tyr Leu Met Lys
                115                 120                 125

Thr Lys Gln Phe Arg Leu Lys Glu Ala Phe Asp Tyr Ile Lys Gln Arg
            130                 135                 140

Arg Ser Met Val Ser Pro Asn Phe Gly Phe Met Gly Gln Leu Leu Gln
145                 150                 155                 160

Tyr Glu Ser Glu Ile Leu Pro Ser Thr Pro Asn
                165                 170
```

<210> SEQ ID NO 21
<211> LENGTH: 180
<212> TYPE: PRT
<213> ORGANISM: Homo sapiens

<400> SEQUENCE: 21

```
Ser Gly Ser Phe Glu Leu Ser Val Gln Asp Leu Asn Asp Leu Leu Ser
1               5                   10                  15

Asp Gly Ser Gly Cys Tyr Ser Leu Pro Ser Gln Pro Cys Asn Glu Val
                20                  25                  30

Thr Pro Arg Ile Tyr Val Gly Asn Ala Ser Val Ala Gln Asp Ile Pro
            35                  40                  45

Lys Leu Gln Lys Leu Gly Ile Thr His Val Leu Asn Ala Ala Glu Gly
50                  55                  60
```

-continued

```
Arg Ser Phe Met His Val Asn Thr Asn Ala Asn Phe Tyr Lys Asp Ser
65                  70                  75                  80

Gly Ile Thr Tyr Leu Gly Ile Lys Ala Asn Asp Thr Gln Glu Phe Asn
                85                  90                  95

Leu Ser Ala Tyr Phe Glu Arg Ala Ala Asp Phe Ile Asp Gln Ala Leu
            100                 105                 110

Ala Gln Lys Asn Gly Arg Val Leu Val His Cys Arg Glu Gly Tyr Ser
        115                 120                 125

Arg Ser Pro Thr Leu Val Ile Ala Tyr Leu Met Met Arg Gln Lys Met
    130                 135                 140

Asp Val Lys Ser Ala Leu Ser Ile Val Arg Gln Asn Arg Glu Ile Gly
145                 150                 155                 160

Pro Asn Asp Gly Phe Leu Ala Gln Leu Cys Gln Leu Asn Asp Arg Leu
                165                 170                 175

Ala Lys Glu Gly
            180

<210> SEQ ID NO 22
<211> LENGTH: 150
<212> TYPE: PRT
<213> ORGANISM: Homo sapiens

<400> SEQUENCE: 22

Met Gly Val Gln Pro Pro Asn Phe Ser Trp Val Leu Pro Gly Arg Leu
1               5                   10                  15

Ala Gly Leu Ala Leu Pro Arg Leu Pro Ala His Tyr Gln Phe Leu Leu
            20                  25                  30

Asp Leu Gly Val Arg His Leu Val Ser Leu Thr Glu Arg Gly Pro Pro
        35                  40                  45

His Ser Asp Ser Cys Pro Gly Leu Thr Leu His Arg Leu Arg Ile Pro
    50                  55                  60

Asp Phe Cys Pro Pro Ala Pro Asp Gln Ile Asp Arg Phe Val Gln Ile
65                  70                  75                  80

Val Asp Glu Ala Asn Ala Arg Gly Glu Ala Val Gly Val His Cys Ala
                85                  90                  95

Leu Gly Phe Gly Arg Thr Gly Thr Met Leu Ala Cys Tyr Leu Val Lys
            100                 105                 110

Glu Arg Gly Leu Ala Ala Gly Asp Ala Ile Ala Glu Ile Arg Arg Leu
        115                 120                 125

Arg Pro Gly Ser Ile Glu Thr Tyr Glu Gln Glu Lys Ala Val Phe Gln
    130                 135                 140

Phe Tyr Gln Arg Thr Lys
145                 150
```

DSP-11 DUAL-SPECIFICITY PHOSPHATASE

CROSS-REFERENCES TO RELATED APPLICATIONS

This application is a continuation of U.S. application Ser. No. 09/619,380 filed Jul. 19, 2000, now U.S. Pat. No. 6,649,391, which application claims the benefit of U.S. Ser. No. 60/144,557, filed Jul. 20, 1999, which are incorperated herein by reference in their entireities

TECHNICAL FIELD

The present invention relates generally to compositions and methods useful for treating conditions associated with defects in cell proliferation, cell differentiation and/or cell survival. The invention is more particularly related to dual-specificity protein phosphatases, and polypeptide variants thereof. The present invention is also related to the use of such polypeptides to identify antibodies and other agents, including small molecules, that modulate signal transduction leading to proliferative responses, cell differentiation and/or cell survival.

BACKGROUND OF THE INVENTION

Mitogen-activated protein kinases (MAP-kinases) are present as components of conserved cellular signal transduction pathways that have a variety of conserved members. MAP-kinases are activated by phosphorylation at a dual phosphorylation motif with the sequence Thr-X-Tyr (by MAP-kinase kinases), in which phosphorylation at the tyrosine and threonine residues is required for activity. Activated MAP-kinases phosphorylate several transduction targets, including transcription factors. Inactivation of MAP-kinases is mediated by dephosphorylation at this site by dual-specificity phosphatases referred to as MAP-kinase phosphatases. In higher eukaryotes, the physiological role of MAP-kinase signaling has been correlated with cellular events such as proliferation, oncogenesis, development and differentiation. Accordingly, the ability to regulate signal transduction via these pathways could lead to the development of treatments and preventive therapies for human diseases associated with MAP-kinase signaling, such as cancer.

Dual-specificity protein tyrosine phosphatases (dual-specificity phosphatases) are phosphatases that dephosphorylate both phosphotyrosine and phosphothreonine/serine residues (Walton et al., *Ann. Rev. Biochem.* 62:101–120, 1993). Several dual-specificity phosphatases that inactivate a MAP-kinase have been identified, including MKP-1 (WO 97/00315; Keyse and Emslie, *Nature* 59:644–647, 1992), MKP-4, MKP-5, MKP-7, Hb5 (WO 97/06245), PAC1 (Ward et al., *Nature* 367:651–654, 1994), HVH2 (Guan and Butch, *J. Biol. Chem.* 270:7197–7203, 1995), PYST1 (Groom et al., *EMBO J.* 15:3621–3632, 1996) and others (see, e.g., WO 95/21923). Expression of certain dual-specificity phosphatases is induced by stress or mitogens, but others appear to be expressed constitutively in specific cell types. The regulation of dual-specificity phosphatase expression and activity is critical for control of MAP-kinase mediated cellular functions, including cell proliferation, cell differentiation and cell survival. For example, dual-specificity phosphatases may function as negative regulators of cell proliferation. It is likely that there are many such dual-specificity phosphatases, with varying specificity with regard to cell type or activation. However, the regulation of dual specificity phosphatases remains poorly understood and only a relatively small number of dual-specificity phosphatases have been identified.

Accordingly, there is a need in the art for an improved understanding of MAP-kinase signaling, and the regulation of dual-specificity phosphatases within MAP-kinase signaling cascades. An increased understanding of dual-specificity phosphatase regulation may facilitate the development of methods for modulating the activity of proteins involved in MAP-kinase cascades, and for treating conditions associated with such cascades. The present invention fulfills these needs and further provides other related advantages.

SUMMARY OF THE INVENTION

Briefly stated, the present invention provides compositions and methods for identifying agents capable of modulating cellular proliferative responses. In one aspect, the present invention provides isolated DSP-11 polypeptides having the sequence of DSP-11 recited in SEQ ID NO:2, or a variant thereof that differs in one or more amino acid deletions, additions, insertions or substitutions at no more than 50% of the residues in SEQ ID NO:2, such that the polypeptide retains the ability to dephosphorylate an activated MAP-kinase.

Within further aspects, the present invention provides an isolated polynucleotide that encodes at least ten consecutive amino acids of a polypeptide having a sequence corresponding to SEQ ID NO:2. In certain embodiments the invention provides an isolated polynucleotide that encodes at least fifteen consecutive amino acids of a polypeptide having a sequence corresponding to SEQ ID NO:2. Certain such polynucleotides encode a DSP-11 polypeptide. Still further, polynucleotides may be antisense polynucleotides that comprise at least 15 consecutive nucleotides complementary to a portion of a DSP-11 polynucleotide and/or that detectably hybridize to the complement of the sequence recited in SEQ ID NO:1 under conditions that include a wash in 0.1×SSC and 0.1% SDS at 50° C. for 15 minutes. Also provided are expression vectors comprising any of the foregoing polynucleotides, and host cells transformed or transfected with such expression vectors.

The present invention further provides, within other aspects, methods for producing a DSP-11 polypeptide, comprising the steps of: (a) culturing a host cell as described above under conditions that permit expression of the DSP-11 polypeptide; and (b) isolating DSP-11 polypeptide from the host cell culture.

Also provided by the present invention are isolated antibodies, and antigen binding fragments thereof, that specifically bind to a DSP-11 polypeptide such as a polypeptide having the sequence of SEQ ID NO:2.

The present invention further provides, within other aspects, pharmaceutical compositions comprising a polypeptide, polynucleotide, antibody or fragment thereof as described above in combination with a physiologically acceptable carrier.

Within further aspects, the present invention provides methods for detecting DSP-11 expression in a sample, comprising: (a) contacting a sample with an antibody or an antigen-binding fragment thereof as described above, under conditions and for a time sufficient to allow formation of an antibody/DSP-11 complex; and (b) detecting the level of antibody/DSP-11 complex.

Within still other aspects, the present invention provides methods for detecting DSP-11 expression in a sample, comprising: (a) contacting a sample with an antisense polynucleotide as described above; and (b) detecting in the sample an amount of DSP-11 polynucleotide that hybridizes to the antisense polynucleotide. The amount of DSP-11 polynucleotide that hybridizes to the antisense polynucleotide may be determined, for example, using polymerase chain reaction or a hybridization assay.

The invention also provides DSP-11 polypeptides useful in screening assays for modulators of enzyme activity and/or substrate binding. Methods are also provided, within other aspects, for screening for an agent that modulates DSP-11 activity, comprising the steps of: (a) contacting a candidate agent with a DSP-11 polypeptide as described above, under conditions and for a time sufficient to permit interaction between the polypeptide and candidate agent; and (b) subsequently evaluating the ability of the polypeptide to dephosphorylate a DSP-11 substrate, relative to a predetermined ability of the polypeptide to dephosphorylate the DSP-11 substrate in the absence of candidate agent. Such methods may be performed in vitro or in a cellular environment (e.g., within an intact cell).

Within further aspects, methods are provided for screening for an agent that modulates DSP-11 activity, comprising the steps of: (a) contacting a candidate agent with a cell comprising a DSP-11 promoter operably linked to a polynucleotide encoding a detectable transcript or protein, under conditions and for a time sufficient to permit interaction between the promoter and candidate agent; and (b) subsequently evaluating the expression of the polynucleotide, relative to a predetermined level of expression in the absence of candidate agent.

Also provided are methods for modulating a proliferative response in a cell, comprising contacting a cell with an agent that modulates DSP-11 activity.

Within further aspects, methods are provided for modulating differentiation of a cell, comprising contacting a cell with an agent that modulates DSP-11 activity.

The present invention further provides methods for modulating cell survival, comprising contacting a cell with an agent that modulates DSP-11 activity.

Within related aspects, the present invention provides methods for treating a patient afflicted with a disorder associated with DSP-11 activity (or treatable by administration of DSP-11), comprising administering to a patient a therapeutically effective amount of an agent that modulates DSP-11 activity. Such disorders include Duchenne muscular dystrophy, cancer, graft-versus-host disease, autoimmune diseases, allergies, metabolic diseases, abnormal cell growth, abnormal cell proliferation and cell cycle abnormalities.

Within further aspects, DSP-11 substrate trapping mutant polypeptides are provided. Such polypeptides differ from the sequence recited in SEQ ID NO:2 in one or more amino acid deletions, additions, insertions or substitutions at no more than 50% of the residues in SEQ ID NO:2, such that the polypeptide binds to a substrate with an affinity that is not substantially diminished relative to DSP-11, and such that the ability of the polypeptide to dephosphorylate a substrate is reduced relative to DSP-11. Within certain specific embodiments, a substrate trapping mutant polypeptide contains a substitution at position 65 or position 95 of SEQ ID NO:2.

The present invention further provides, within other aspects, methods for screening a molecule for the ability to interact with DSP-11, comprising the steps of: (a) contacting a candidate molecule with a polypeptide as described above under conditions and for a time sufficient to permit the candidate molecule and polypeptide to interact; and (b) detecting the presence or absence of binding of the candidate molecule to the polypeptide. The step of detecting may comprise, for example, an affinity purification step, a yeast two hybrid screen or a screen of a phage display library.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 presents a cDNA sequence for DSP-11 (SEQ ID NO:1), with the start and stop codons indicated in bold.

FIG. 2 presents the predicted amino acid sequence of DSP-11 (SEQ ID NO:2).

FIG. 3 is a sequence alignment showing sequence similarity between DSP-11 and other MAP-kinase phosphatases (SEQ ID NOS: 14–22).

FIG. 5 presents cDNA coding sequence for a murine DSP-11 variant (SEQ ID NO:12).

FIG. 6 presents the predicted amino acid sequence of a murine DSP-11 variant (SEQ ID NO:13).

DETAILED DESCRIPTION OF THE INVENTION

Figure 4:
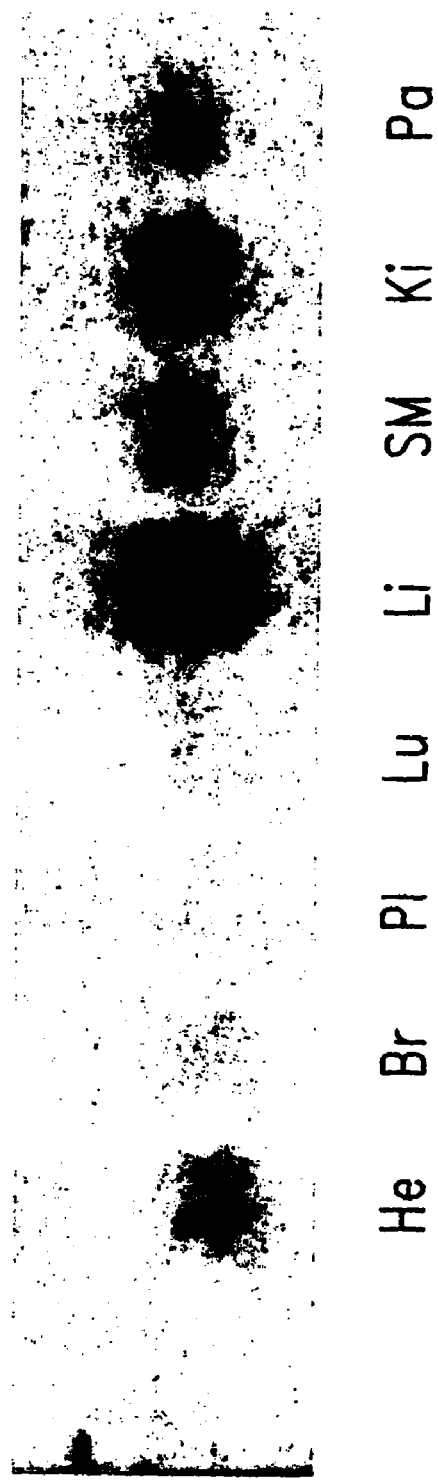
FIG. 4 shows northern blot hybridization using a $^{32}$P-labeled full length DSP-11 encoding nucleic acid sequence as probe. Blot contained human polyA+ RNA from various tissue types as follows: He, heart; Br, brain; Pl, placenta; Lu, lung; Li, liver; SM, skeletal muscle; Ki, kidney; Pa, pancreas.

As noted above, the present invention is generally directed to compositions and methods for modulating (i.e., stimulating or inhibiting) cellular proliferative responses, in vitro and in vivo. In particular, the present invention provides a dual-specificity phosphatase DSP-11 (FIGS. 1–2; SEQ ID NOs:1–2), as well as variants thereof and antibodies that specifically bind DSP-11. Also provided herein are methods for using such compounds for screens, detection assays and related therapeutic uses.

DSP-11 POLYPEPTIDES AND POLYNUCLEOTIDES

As used herein, the term "DSP-11 polypeptide" refers to a polypeptide that comprises a DSP-11 sequence as provided herein or a variant of such a sequence. Such polypeptides are capable of dephosphorylating both tyrosine and threonine/serine residues in a DSP-11 substrate, with an activity that is not substantially diminished relative to that of a full length native DSP-11. DSP-11 substrates include activated (i.e., phosphorylated) MAP-kinases. Other substrates may be identified using substrate trapping mutants, as described herein, and include polypeptides having one or more phosphorylated tyrosine, threonine and/or serine residues.

DSP-11 polypeptide variants within the scope of the present invention may contain one or more substitutions, deletions, additions and/or insertions. For certain DSP-11 variants, the ability of the variant to dephosphorylate tyrosine and threonine residues within a DSP-11 substrate is not substantially diminished. The ability of such a DSP-11 variant to dephosphorylate tyrosine and threonine residues within a DSP-11 substrate may be enhanced or unchanged, relative to a native DSP-11, or may be diminished by less than 50%, and preferably less than 20%, relative to native DSP-11. Such variants may be identified using the representative assays provided herein.

Also contemplated by the present invention are modified forms of DSP-11 in which a specific function is disabled. For example, such proteins may be constitutively active or inactive, or may display altered binding or catalytic properties. Such altered proteins may be generated using well known techniques, and the altered function confirmed using screens such as those provided herein. Certain modified DSP-11 polypeptides are known as "substrate trapping mutants." Such polypeptides retain the ability to bind a substrate (i.e., $K_m$ is not substantially diminished), but display a reduced ability to dephosphorylate a substrate (i.e., $k_{cat}$ is reduced, preferably to less than 1 per minute). Further, the stability of the substrate trapping mutant/substrate complex should not be substantially diminished, relative to the stability of a DSP-11/substrate complex. Complex stability may be assessed based on the association constant ($K_a$). Determination of $K_m$, $k_{cat}$ and $K_a$ may be readily accomplished using standard techniques known in the art (see, e.g., WO 98/04712; Lehninger, Biochemistry, 1975 Worth Publishers, NY) and assays provided herein. Substrate trapping mutants may be generated, for example, by modifying DSP-11 with an amino acid substitution at position 65 or position 95 (e.g., by replacing the amino acid aspartate at position 65 with an alanine residue, or by replacing the cysteine at residue 95 with a serine). Substrate trapping mutants may be used, for example, to identify DSP-11 substrates. Briefly, the modified DSP-11 may be contacted with a candidate substrate (alone or within a mixture of proteins, such as a cell extract) to permit the formation of a substrate/DSP-11 complex. The complex may then be isolated by conventional techniques to permit the isolation and characterization of substrate. The preparation and use of substrate trapping mutants is described, for example, within PCT Publication No. WO 98/04712.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes.

In general, modifications may be more readily made in non-critical regions, which are regions of the native sequence that do not substantially change the activity of DSP-11. Non-critical regions may be identified by modifying the DSP-11 sequence in a particular region and assaying the ability of the resulting variant in a phosphatase assay, as described herein. Preferred sequence modifications are made so as to retain the active site domain (VGVHCALGFGRTGTMLACYLV; SEQ ID NO:3). Within certain preferred embodiments, such modifications affect interactions between DSP-11 and cellular components other than DSP-11 substrates. However, substitutions may also be made in critical regions of the native protein, provided that the resulting variant substantially retains the ability to stimulate substrate dephosphorylation. Within certain embodiments, a variant contains substitutions, deletions, additions and/or insertions at no more than 50%, preferably no more than 25%, of the amino acid residues.

Variants may also (or alternatively) be modified by, for example, the deletion or addition of amino acids that have minimal influence on the activity of the polypeptide. In particular, variants may contain additional amino acid sequences at the amino and/or carboxy termini. Such sequences may be used, for example, to facilitate purification or detection of the polypeptide.

DSP-11 polypeptides may be prepared using any of a variety of well known techniques. Recombinant polypeptides encoded by DNA sequences as described below may be readily prepared from the DNA sequences using any of a variety of expression vectors known to those having ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells (including mammalian cells), and forms that differ in glycosylation may be generated by varying the host cell or post-isolation processing. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic procedures, using techniques well known to those having ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin-Elmer, Inc., Applied BioSystems Division (Foster City, Calif.), and may be operated according to the manufacturer's instructions.

A "DSP-11 polynucleotide" is any polynucleotide that encodes at least a portion of a DSP-11 polypeptide or a variant thereof, or that is complementary to such a polynucleotide. Preferred polynucleotides comprise at least 15 consecutive nucleotides, preferably at least 30 consecutive nucleotides, that encode a DSP-11 polypeptide or that are complementary to such a sequence. Certain polynucleotides encode a DSP-11 polypeptide; others may find use as probes, primers or antisense oligonucleotides, as described below. Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

DSP-11 polynucleotides may comprise a native sequence (i.e., an endogenous DSP-11 sequence or a portion or splice variant thereof) or may comprise a variant of such a sequence. Polynucleotide variants may contain one or more substitutions, additions, deletions and/or insertions such that the activity of the encoded polypeptide is not substantially diminished, as described above. The effect on the activity of the encoded polypeptide may generally be assessed as described herein. Variants preferably exhibit at least about 70% identity, more preferably at least about 80% identity and most preferably at least about 90% identity to a polynucleotide sequence that encodes a native DSP-11 or a portion thereof. The percent identity may be readily determined by comparing sequences using computer algorithms well known to those having ordinary skill in the art, such as Align or the BLAST algorithm (Altschul, *J. Mol. Biol.* 219:555–565, 1991; Henikoff and Henikoff, *Proc. Natl. Acad. Sci. USA* 89:10915–10919, 1992), which is available at the NCBI website (http://www/ncbi.nlm.nih.gov/cgi-bin/BLAST). Default parameters may be used. Certain variants are substantially homologous to a native gene. Such polynucleotide variants are capable of hybridizing under moderately stringent conditions to a naturally occurring DNA or RNA sequence encoding a native DSP-11 (or a complementary sequence). Suitable moderately stringent conditions include, for example, prewashing in a solution of 5×SSC, 0.5% SDS, 1.0 mM EDTA (pH 8.0); hybridizing at 50° C.–70° C., 5×SSC for 1–16 hours; followed by washing once or twice at 22–65° C. for 20–40 minutes with one or more each of 2×, 0.5× and 0.2×SSC containing 0.05–0.1% SDS. For additional stringency, conditions may include a wash in 0.1×SSC and 0.1% SDS at 50–60° C. for 15–40 minutes. As known to those having ordinary skill in the art, variations in stringency of hybridization conditions may be achieved by altering the time, temperature and/or concentration of the solutions used for prehybridization, hybridization and wash steps, and suitable conditions may also depend in part on the particular nucleotide sequences of the probe used, and of the blotted, proband nucleic acid sample. Accordingly, it will be appreciated that suitably stringent conditions can be readily selected without undue experimentation where a desired selectivity of the probe is identified, based on its ability to hybridize to one or more certain proband sequences while not hybridizing to certain other proband sequences.

It will also be appreciated by those having ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention.

Polynucleotides may be prepared using any of a variety of techniques. For example, a polynucleotide may be amplified from cDNA prepared from a suitable cell or tissue type, such as human brain, testis, kidney or skeletal muscle. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., human brain, testis, kidney, liver or skeletal muscle cDNA) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library may then be screened by hybridizing filters containing denatured bacterial colonies (or lawns containing phage plaques) with the labeled probe (see e.g., Sambrook et al., *Molecular Cloning: A Laboratory Manual,* Cold Spring Harbor Laboratories, Cold Spring Harbor, N.Y., 1989). Hybridizing colonies or plaques are selected and expanded, and the DNA is isolated for further analysis. Clones may be analyzed to determine the amount of additional sequence by, for example, PCR using a primer from the partial sequence and a primer from the vector. Restriction maps and partial sequences may be generated to identify one or more overlapping clones. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. One such technique is known as "rapid amplification of cDNA ends" or RACE. This technique involves the use of an internal primer and an external primer, which hybridizes to a polyA region or vector sequence, to identify sequences that are 5' and 3' of a known sequence. Any of a variety of commercially available kits may be used to perform the amplification step. Primers may be designed using, for example, software well known in the art. Primers are preferably 17–32 nucleotides in length, have a GC content of at least 40% and anneal to the target sequence at temperatures of about 54° C. to 72° C. The amplified region may be sequenced as described above, and overlapping sequences assembled into a contiguous sequence.

Figure 3:
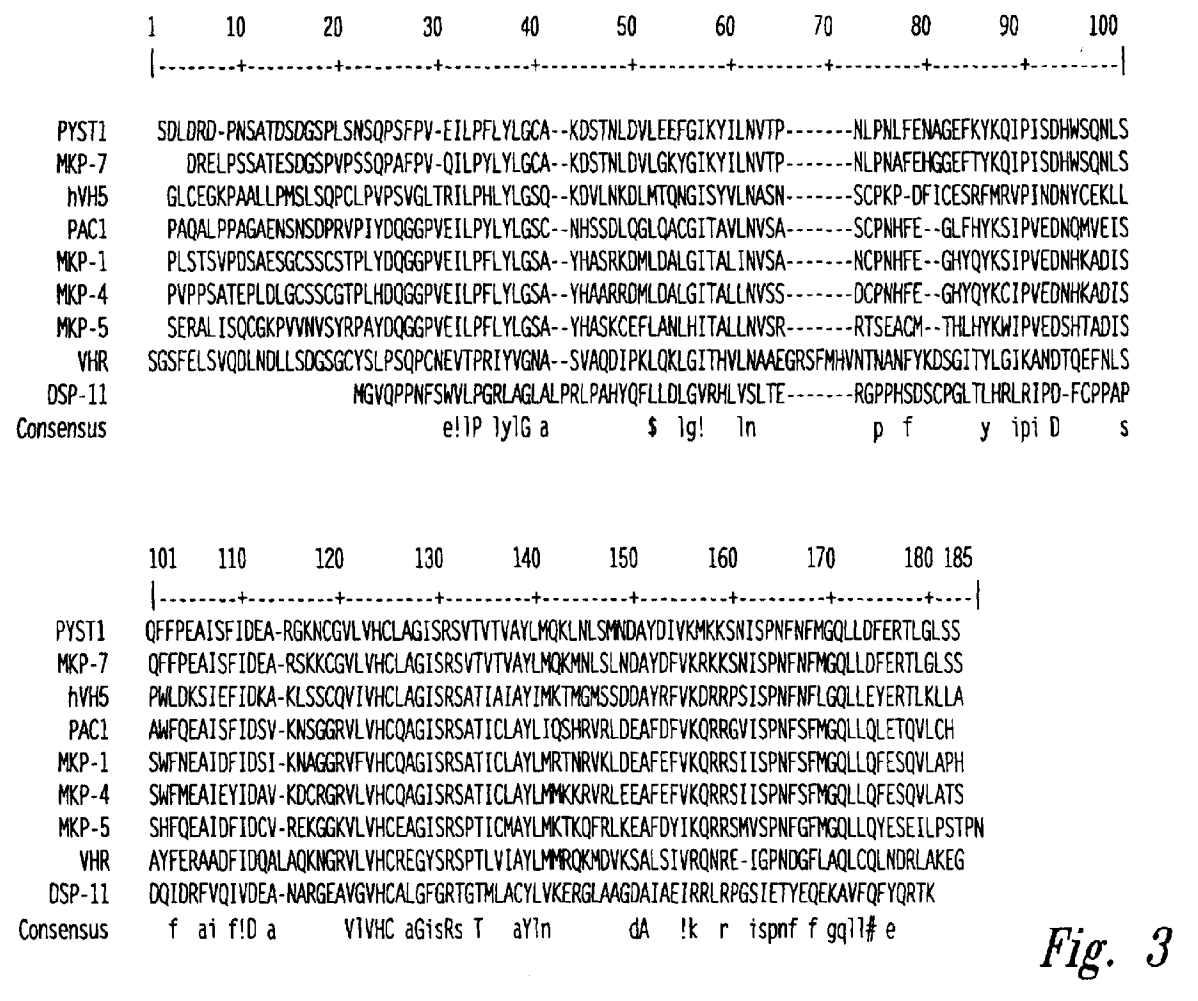

A cDNA sequence encoding DSP-11 is provided in FIG. 1 (SEQ ID NO:1), and the predicted amino acid sequence is provided in FIG. 2 (SEQ ID NO:2). The DSP-11 active site (VGVHCALGFGRTGTMLACYLV; SEQ ID NO:3), is located at positions 91 through 110 of SEQ ID NO:2. Sequence information immediately adjacent to this site was used to design 5' and 3' RACE reactions with human kidney cDNA to identify a 450 base pair cDNA that corresponds to a mRNA that displays a higher abundance in kidney and liver RNA. This cDNA encodes a protein of 150 amino acids that is referred to herein as dual specificity phosphatase-11, or DSP-11. DSP-11 shows significant homology to other MAP-kinase phosphatases, as shown by the sequence comparison presented in FIG. 3.

DSP-11 polynucleotide variants may generally be prepared by any method known in the art, including, for example, solid phase chemical synthesis. Modifications in a polynucleotide sequence may also be introduced using standard mutagenesis techniques, such as oligonucleotide-directed site-specific mutagenesis. Alternatively, RNA molecules may be generated by in vitro or in vivo transcription of DNA sequences encoding DSP-11, or a portion thereof, provided that the DNA is incorporated into a vector with a suitable RNA polymerase promoter (such as T7 or SP6). Certain polynucleotides may be used to prepare an encoded polypeptide, as described herein. In addition, or alternatively, a polynucleotide may be administered to a patient such that the encoded polypeptide is generated in vivo.

A polynucleotide that is complementary to at least a portion of a coding sequence (e.g., an antisense polynucleotide or a ribozyme) may also be used as a probe or primer, or to modulate gene expression. Identification of oligonucleotides and ribozymes for use as antisense agents, and DNA encoding genes for their targeted delivery, involve methods well known in the art. For example, the desirable properties, lengths and other characteristics of such oligonucleotides are well known. Antisense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., *Tetrahedron Lett.* 28:3539–3542 (1987); Miller et al., *J. Am. Chem. Soc.* 93:6657–6665 (1971); Stec et al., *Tetrahedron Lett.* 26:2191–2194 (1985); Moody et al., *Nucl. Acids Res.* 12:4769–4782 (1989); Uznanski et al., *Nucl. Acids Res.* (1989); Letsinger et al., *Tetrahedron* 40:137–143 (1984); Eckstein, *Annu. Rev. Biochem.* 54:367–402 (1985); Eckstein, *Trends Biol. Sci.* 14:97–100 (1989); Stein In: *Oligodeoxynucleotides. Antisense Inhibitors of Gene Expression,* Cohen, Ed, Macmillan Press, London, pp. 97–117 (1989); Jager et al., *Biochemistry* 27:7237–7246 (1988)).

Antisense polynucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. No. 5,168,053 to Altman et al.; U.S. Pat. No. 5,190,931 to Inouye, U.S. Pat. No. 5,135,917 to Burch; U.S. Pat. No. 5,087,617 to Smith and Clusel et al. (1993) *Nucl. Acids Res.* 21:3405–3411, which describes dumbbell antisense oligonucleotides). Triplex molecules refer to single DNA strands that bind duplex DNA forming a colinear triplex molecule, thereby preventing transcription (see, e.g., U.S. Pat. No. 5,176,996 to Hogan et al., which describes methods for making synthetic oligonucleotides that bind to target sites on duplex DNA).

Particularly useful antisense nucleotides and triplex molecules are molecules that are complementary to or bind the sense strand of DNA or mRNA that encodes a DSP-11 polypeptide or a protein mediating any other process related to expression of endogenous DSP-11, such that inhibition of translation of mRNA encoding the DSP-11 polypeptide is effected. cDNA constructs that can be transcribed into antisense RNA may also be introduced into cells or tissues to facilitate the production of antisense RNA. Antisense technology can be used to control gene expression through interference with binding of polymerases, transcription factors or other regulatory molecules (see Gee et al., In Huber and Carr, *Molecular and Immunologic Approaches,* Futura Publishing Co. (Mt. Kisco, N.Y.; 1994)). Alternatively, an antisense molecule may be designed to hybridize with a control region of a DSP-11 gene (e.g., promoter, enhancer or transcription initiation site), and block transcription of the gene; or to block translation by inhibiting binding of a transcript to ribosomes.

The present invention also contemplates DSP-11-specific ribozymes. A ribozyme is an RNA molecule that specifically cleaves RNA substrates, such as mRNA, resulting in specific inhibition or interference with cellular gene expression. There are at least five known classes of ribozymes involved in the cleavage and/or ligation of RNA chains. Ribozymes can be targeted to any RNA transcript and can catalytically cleave such transcripts (see, e.g., U.S. Pat. No. 5,272,262; U.S. Pat. No. 5,144,019; and U.S. Pat. Nos. 5,168,053, 5,180,818, 5,116,742 and 5,093,246 to Cech et al.). Any DSP-11 mRNA-specific ribozyme, or a nucleic acid encoding such a ribozyme, may be delivered to a host cell to effect inhibition of DSP-11 gene expression. Ribozymes may therefore be delivered to the host cells by DNA encoding the ribozyme linked to a eukaryotic promoter, such as a eukaryotic viral promoter, such that upon introduction into the nucleus, the ribozyme will be directly transcribed.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a suitable vector contains an origin of replication functional in at least one organism, convenient restriction endonuclease sites and one or more selectable markers. Other elements will depend upon the desired use, and will be apparent to those having ordinary skill in the art.

Within certain embodiments, polynucleotides may be formulated so as to permit entry into a cell of a mammal, and expression therein. Such formulations are particularly useful for therapeutic purposes, as described below. Those having ordinary skill in the art will appreciate that there are many ways to achieve expression of a polynucleotide in a target cell, and any suitable method may be employed. For example, a polynucleotide may be incorporated into a viral vector using well known techniques. A viral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those having ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Within other aspects, a DSP-11 promoter may be isolated using standard techniques. The present invention provides nucleic acid molecules comprising such a promoter or one or more cis- or trans-acting regulatory elements thereof. Such regulatory elements may enhance or suppress expression of DSP-11. A 5' flanking region may be generated using standard techniques, based on the genomic sequence provided herein. If necessary, additional 5' sequences may be generated using PCR-based or other standard methods. The 5' region may be subcloned and sequenced using standard methods. Primer extension and/or RNase protection analyses may be used to verify the transcriptional start site deduced from the cDNA.

To define the boundary of the promoter region, putative promoter inserts of varying sizes may be subcloned into a heterologous expression system containing a suitable reporter gene without a promoter or enhancer. Suitable reporter genes may include genes encoding luciferase, beta-galactosidase, chloramphenicol acetyl transferase, secreted alkaline phosphatase or the Green Fluorescent Protein gene. Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of DSP-11 expression. In general, the construct with the minimal 5' flanking region showing the highest level of expression of reporter gene is identified as the promoter. Such promoter regions may be linked to a reporter gene and used to evaluate agents for the ability to modulate DSP-11 transcription.

Once a functional promoter is identified, cis- and trans-acting elements may be located. Cis-acting sequences may generally be identified based on homology to previously characterized transcriptional motifs. Point mutations may then be generated within the identified sequences to evaluate the regulatory role of such sequences. Such mutations may be generated using site-specific mutagenesis techniques or a PCR-based strategy. The altered promoter is then cloned into a reporter gene expression vector, as described above, and the effect of the mutation on reporter gene expression is evaluated.

The present invention also contemplates the use of allelic variants of DSP-11, as well as DSP-11 sequences from other organisms. Such sequences may generally be identified based upon similarity to the sequences provided herein (e.g., using hybridization techniques) and based upon the presence of DSP-11 activity, using an assay provided herein.

In general, polypeptides and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

ASSAYS FOR DETECTING DSP-11 ACTIVITY

According to the present invention, substrates of DSP-11 may include full length tyrosine phosphorylated proteins and polypeptides as well as fragments (e.g., portions), derivatives or analogs thereof that can be phosphorylated at a tyrosine residue and that may, in certain preferred embodiments, also be able to undergo phosphorylation at a serine or a threonine residue. Such fragments, derivatives and analogs include any naturally occurring or artificially engineered DSP-11 substrate polypeptide that retains at least the biological function of interacting with a DSP-11 as provided herein, for example by forming a complex with a DSP-11. A fragment, derivative or analog of a DSP-11 substrate polypeptide, including substrates that are fusion proteins, may be (i) one in which one or more of the amino acid residues are substituted with a conserved or non-conserved amino acid residue (preferably a conserved amino acid residue), and such substituted amino acid residue may or may not be one encoded by the genetic code, or (ii) one in which one or more of the amino acid residues includes a substituent group, or (iii) one in which the substrate polypeptide is fused with another compound, such as a compound to increase the half-life of the polypeptide (e.g., polyethylene glycol) or a detectable moiety such as a reporter molecule, or (iv) one in which additional amino acids are fused to the substrate polypeptide, including amino acids that are employed for purification of the substrate polypeptide or a proprotein sequence. Such fragments, derivatives and analogs are deemed to be within the scope of those skilled in the art. In preferred embodiment, a MAP-kinase polypeptide is a substrate for use as provided herein.

DSP-11 polypeptide variants may be tested for DSP-11 activity using any suitable assay for MAP-kinase phosphatase activity. Such assays may be performed in vitro or within a cell-based assay. For example, a MAP-kinase may be obtained in inactive form from Upstate Biotechnology (Lake Placid, N.Y.; catalog number 14–198), for use as a DSP-11 substrate as provided herein. Phosphorylation of the MAP-kinase can be performed using well known techniques (such as those described by Zheng and Guan, *J. Biol. Chem.* 268:16116–16119, 1993) using the MAP-kinase kinase MEK-1 (available from Upstate Biotechnology; cat. no. 14–206).

For example, [$^{32}$P]-radiolabeled substrate (e.g., MAP-kinase) may be used for the kinase reaction, resulting in radiolabeled, activated MAP-kinase. A DSP-11 polypeptide may then be tested for the ability to dephosphorylate an activated MAP-kinase by contacting the DSP-11 polypeptide with the MAP-kinase under suitable conditions (e.g., Tris, pH 7.5, 1 mM EDTA, 1 mM dithiothreitol, 1 mg/mL bovine serum albumin for 10 minutes at 30° C.; or as described by Zheng and Guan, *J. Biol. Chem.* 268:16116–16119, 1993). Dephosphorylation of the MAP-kinase may be detected using any of a variety of assays, such as a coupled kinase assay (evaluating phosphorylation of a MAP-kinase substrate using any assay generally known in the art) or directly, based on (1) the loss of radioactive phosphate groups. (e.g., by gel electrophoresis, followed by autoradiography); (2) the shift in electrophoretic mobility following dephosphorylation; (3) the loss of reactivity with an antibody specific for phosphotyrosine or phosphothreonine; or (4) a phosphoamino acid analysis of the MAP-kinase. Certain assays may generally be performed as described by Ward et al., *Nature* 367:651–654, 1994 or Alessi et al., *Oncogene* 8:2015–2020, 1993. In general, contact of 500 pg–50 ng of DSP-11 polypeptide with 100 ng–100 µg activated MAP-kinase should result in a detectable dephosphorylation of the MAP-kinase, typically within 20–30 minutes. Within certain embodiments, 0.01–10 units/mL (preferably about 0.1 units/mL, where a unit is an amount sufficient to dephosphorylate 1 nmol substrate per minute) DSP-11 polypeptide may be contacted with 0.1–10 µM (preferably about 1 µM) activated MAP-kinase to produce a detectable dephosphorylation of a MAP-kinase. Preferably, a DSP-11 polypeptide results in a dephosphorylation of a MAP-kinase or a phosphorylated substrate (such as a tyrosine and/or serine-phosphorylated peptide) that is at least as great as the dephosphorylation observed in the presence of a comparable amount of native human DSP-11. It will be apparent that other substrates identified using a substrate trapping mutant as described herein may be substituted for the MAP-kinase within such assays.

ANTIBODIES AND ANTIGEN-BINDING FRAGMENTS

Also contemplated by the present invention are peptides, polypeptides, and other non-peptide molecules that specifically bind to a DSP-11. As used herein, a molecule is said to "specifically bind" to a DSP-11 if it reacts at a detectable level with DSP-11, but does not react detectably with peptides containing an unrelated sequence, or a sequence of a different phosphatase. Preferred binding molecules include antibodies, which may be, for example, polyclonal, monoclonal, single chain, chimeric, anti-idiotypic, or CDR-grafted immunoglobulins, or fragments thereof, such as proteolytically generated or recombinantly produced immunoglobulin F(ab')$_2$, Fab, Fv, and Fd fragments. Certain preferred antibodies are those antibodies that inhibit or block DSP-11 activity within an in vitro assay, as described herein. Binding properties of an antibody to DSP-11 may generally be assessed using immunodetection methods including, for example, an enzyme-linked immunosorbent assay (ELISA), immunoprecipitation, immunoblotting and the like, which may be readily performed by those having ordinary skill in the art.

Methods well known in the art may be used to generate antibodies, polyclonal antisera or monoclonal antibodies that are specific for a DSP-11. Antibodies also may be produced as genetically engineered immunoglobulins (Ig) or Ig fragments designed to have desirable properties. For example, by way of illustration and not limitation, antibodies may include a recombinant IgG that is a chimeric fusion protein having at least one variable (V) region domain from a first mammalian species and at least one constant region domain from a second, distinct mammalian species. Most commonly, a chimeric antibody has murine variable region sequences and human constant region sequences. Such a murine/human chimeric immunoglobulin may be "humanized" by grafting the complementarity determining regions (CDRs) derived from a murine antibody, which confer binding specificity for an antigen, into human-derived V region framework regions and human-derived constant regions. Fragments of these molecules may be generated by proteolytic digestion, or optionally, by proteolytic digestion followed by mild reduction of disulfide bonds and alkylation. Alternatively, such fragments may also be generated by recombinant genetic engineering techniques.

As used herein, an antibody is said to be "immunospecific" or to "specifically bind" a DSP-11 polypeptide if it reacts at a detectable level with DSP-11, preferably with an affinity constant, $K_a$, of greater than or equal to about $10^4$ $M^{-1}$, more preferably of greater than or equal to about $10^5$ $M^{-1}$, more preferably of greater than or equal to about $10^6$ $M^{-1}$, and still more preferably of greater than or equal to about $10^7$ $M^{-1}$. Affinities of binding partners or antibodies can be readily determined using conventional techniques, for example, those described by Scatchard et al. (*Ann. N.Y. Acad. Sci. USA* 51:660 (1949)) or by surface plasmon resonance (BIAcore, Biosensor, Piscataway, N.J.). See, e.g., Wolff et al., *Cancer Res.* 53:2560–2565 (1993).

Antibodies may generally be prepared by any of a variety of techniques known to those having ordinary skill in the art. See, e.g., Harlow et al., *Antibodies: A Laboratory Manual*, Cold Spring Harbor Laboratory (1988). In one such technique, an animal is immunized with DSP-11 as an antigen to generate polyclonal antisera. Suitable animals include, for example, rabbits, sheep, goats, pigs, cattle, and may also include smaller mammalian species, such as mice, rats, and hamsters, or other species.

An immunogen may be comprised of cells expressing DSP-11, purified or partially purified DSP-11 polypeptides or variants or fragments (e.g., peptides) thereof, or DSP-11 peptides. DSP-11 peptides may be generated by proteolytic cleavage or may be chemically synthesized. For instance, nucleic acid sequences encoding DSP-11 polypeptides are provided herein, such that those skilled in the art may routinely prepare these polypeptides for use as immunogens. Polypeptides or peptides useful for immunization may also be selected by analyzing the primary, secondary, and tertiary structure of DSP-11 according to methods known to those skilled in the art, in order to determine amino acid sequences more likely to generate an antigenic response in a host animal. See, e.g., Novotny, 1991 *Mol. Immunol.* 28:201–207; Berzofsky, 1985 *Science* 229:932–40.

Preparation of the immunogen for injection into animals may include covalent coupling of the DSP-11 polypeptide (or variant or fragment thereof), to another immunogenic protein, for example, a carrier protein such as keyhole limpet hemocyanin (KLH) or bovine serum albumin (BSA). In addition, the DSP-11 peptide, polypeptide, or DSP-11-expressing cells to be used as immunogen may be emulsified in an adjuvant. See, e.g., Harlow et al., *Antibodies: A Laboratory Manual*, Cold Spring Harbor Laboratory (1988). In general, after the first injection, animals receive one or more booster immunizations according to a preferred schedule that may vary according to, inter alia, the antigen, the adjuvant (if any) and/or the particular animal species. The immune response may be monitored by periodically bleeding the animal, separating the sera out of the collected blood, and analyzing the sera in an immunoassay, such as an ELISA or Ouchterlony diffusion assay, or the like, to determine the specific antibody titer. Once an antibody titer is established, the animals may be bled periodically to accumulate the polyclonal antisera. Polyclonal antibodies that bind specifically to the DSP-11 polypeptide or peptide may then be purified from such antisera, for example, by affinity chromatography using protein A, or the DSP-11 polypeptide, immobilized on a suitable solid support.

Monoclonal antibodies that specifically bind to DSP-11 polypeptides or fragments or variants thereof, and hybridomas, which are immortal eukaryotic cell lines, that produce monoclonal antibodies having the desired binding specificity, may also be prepared, for example, using the technique of Kohler and Milstein (*Nature*, 256:495–497; 1976, *Eur. J Immunol.* 6:511–519 (1975)) and improvements thereto. An animal—for example, a rat, hamster, or preferably mouse-is immunized with a DSP-11 immunogen prepared as described above. Lymphoid cells that include antibody-forming cells, typically spleen cells, are obtained from an immunized animal and may be immortalized by fusion with a drug-sensitized myeloma (e.g., plasmacytoma) cell fusion partner, preferably one that is syngeneic with the immunized animal and that optionally has other desirable properties (e.g., inability to express endogenous Ig gene products). The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells, but not unfused myeloma cells. A preferred selection media is HAT (hypoxanthine, aminopterin, thymidine). After a sufficient time, usually about one to two weeks, colonies of cells are observed. Single colonies are isolated, and antibodies produced by the cells may be tested for binding activity to the DSP-11 polypeptide, or variant or fragment thereof. Hybridomas producing monoclonal antibodies with high affinity and specificity for a DSP-11 antigen are preferred. Hybridomas that produce monoclonal antibodies that specifically bind to a DSP-11 polypeptide or variant or fragment thereof are therefore contemplated by the present invention.

Monoclonal antibodies may be isolated from the supernatants of hybridoma cultures. An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Contaminants may be removed from the subsequently (usually within 1–3 weeks) harvested ascites fluid by conventional techniques, such as chromatography, gel filtration, precipitation, extraction, or the like. For example, antibodies may be purified by affinity chromatography using an appropriate ligand selected based on particular properties of the monoclonal antibody (e.g., heavy or light chain isotype, binding specificity, etc.). Examples of a suitable ligand, immobilized on a solid support, include Protein A, Protein G, an anti-constant region (light chain or heavy chain) antibody, an anti-idiotype antibody and a DSP-11 polypeptide or fragment or variant thereof.

Human monoclonal antibodies may be generated by any number of techniques with which those having ordinary skill in the art will be familiar. Such methods include but are not limited to, Epstein Barr Virus (EBV) transformation of human peripheral blood cells (e.g., containing B lymphocytes), in vitro immunization of human B cells, fusion of spleen cells from immunized transgenic mice carrying human immunoglobulin genes inserted by yeast artificial chromosomes (YAC), isolation from human immunoglobulin V region phage libraries, or other procedures as known in the art and based on the disclosure herein.

For example, one method for generating human monoclonal antibodies includes immortalizing human peripheral blood cells by EBV transformation. See, e.g., U.S. Pat. No. 4,464,456. An immortalized cell line producing a monoclonal antibody that specifically binds to a DSP-11 polypeptide (or a variant or fragment thereof) can be identified by immunodetection methods as provided herein, for example, an ELISA, and then isolated by standard cloning techniques. Another method to generate human monoclonal antibodies, in vitro immunization, includes priming human splenic B cells with antigen, followed by fusion of primed B cells with a heterohybrid fusion partner. See, e.g., Boerner et al., 1991 *J. Immunol.* 147:86–95.

Still another method for the generation of human DSP-11-specific monoclonal antibodies and polyclonal antisera for use in the present invention relates to transgenic mice. See, e.g., U.S. Pat. No. 5,877,397; Bruggemann et al., 1997 *Curr. Opin. Biotechnol.* 8:455–58; Jakobovits et al., 1995 *Ann. N.Y. Acad. Sci.* 764:525–35. In these mice, human immunoglobulin heavy and light chain genes have been artificially introduced by genetic engineering in germline configuration, and the endogenous murine immunoglobulin genes have been inactivated. See, e.g., Bruggemann et al., 1997 *Curr. Opin. Biotechnol.* 8:455–58. For example, human immunoglobulin transgenes may be mini-gene constructs, or transloci on yeast artificial chromosomes, which undergo B cell-specific DNA rearrangement and hypermutation in the mouse lymphoid tissue. See, Bruggemann et al., 1997 *Curr. Opin. Biotechnol.* 8:455–58. Human monoclonal antibodies specifically binding to DSP-11 may be obtained by immunizing the transgenic animals, fusing spleen cells with myeloma cells, selecting and then cloning cells producing antibody, as described above. Polyclonal sera containing human antibodies may also be obtained from the blood of the immunized animals.

Chimeric antibodies, specific for a DSP-11, including humanized antibodies, may also be generated according to the present invention. A chimeric antibody has at least one constant region domain derived from a first mammalian species and at least one variable region domain derived from a second, distinct mammalian species. See, e.g., Morrison et al., 1984, *Proc. Natl. Acad. Sci. USA*, 81:6851–55. In preferred embodiments, a chimeric antibody may be constructed by cloning the polynucleotide sequence that encodes at least one variable region domain derived from a non-human monoclonal antibody, such as the variable region derived from a murine, rat, or hamster monoclonal antibody, into a vector containing a nucleic acid sequence that encodes at least one human constant region. See, e.g., Shin et al., 1989 *Methods Enzymol.* 178:459–76; Walls et al., 1993 *Nucleic Acids Res.* 21:2921–29. By way of example, the polynucleotide sequence encoding the light chain variable region of a murine monoclonal antibody may be inserted into a vector containing a nucleic acid sequence encoding the human kappa light chain constant region sequence. In a separate vector, the polynucleotide sequence encoding the heavy chain variable region of the monoclonal antibody may be cloned in frame with sequences encoding the human IgG1 constant region. The particular human constant region selected may depend upon the effector functions desired for the particular antibody (e.g., complement fixing, binding to a particular Fc receptor, etc.). Another method known in the art for generating chimeric antibodies is homologous recombination (e.g., U.S. Pat. No. 5,482,856). Preferably, the vectors will be transfected into eukaryotic cells for stable expression of the chimeric antibody.

A non-human/human chimeric antibody may be further genetically engineered to create a "humanized" antibody. Such a humanized antibody may comprise a plurality of CDRs derived from an immunoglobulin of a non-human mammalian species, at least one human variable framework region, and at least one human immunoglobulin constant region. Humanization may in certain embodiments provide an antibody that has decreased binding affinity for a DSP-11 when compared, for example, with either a non-human monoclonal antibody from which a DSP-11 binding variable region is obtained, or a chimeric antibody having such a V region and at least one human C region, as described above. Useful strategies for designing humanized antibodies may therefore include, for example by way of illustration and not limitation, identification of human variable framework regions that are most homologous to the non-human framework regions of the chimeric antibody. Without wishing to be bound by theory, such a strategy may increase the likelihood that the humanized antibody will retain specific binding affinity for a DSP-11, which in some preferred embodiments may be substantially the same affinity for a DSP-11 polypeptide or variant or fragment thereof, and in certain other preferred embodiments may be a greater affinity for DSP-11. See, e.g., Jones et al., 1986 *Nature* 321:522–25; Riechmann et al., 1988 *Nature* 332:323–27. Designing such a humanized antibody may therefore include determining CDR loop conformations and structural determinants of the non-human variable regions, for example, by computer modeling, and then comparing the CDR loops and determinants to known human CDR loop structures and determinants. See, e.g., Padlan et al., 1995 *FASEB* 9:133–39; Chothia et al., 1989 *Nature,* 342:377–383. Computer modeling may also be used to compare human structural templates selected by sequence homology with the non-human variable regions. See, e.g., Bajorath et al., 1995 *Ther. Immunol.* 2:95–103; EP-0578515-A3. If humanization of the non-human CDRs results in a decrease in binding affinity, computer modeling may aid in identifying specific amino acid residues that could be changed by site-directed or other mutagenesis techniques to partially, completely or supra-optimally (i.e., increase to a level greater than that of the non-humanized antibody) restore affinity. Those having ordinary skill in the art are familiar with these techniques, and will readily appreciate numerous variations and modifications to such design strategies.

Within certain embodiments, the use of antigen-binding fragments of antibodies may be preferred. Such fragments include Fab fragments or F(ab')$_2$ fragments, which may be prepared by proteolytic digestion with papain or pepsin, respectively. The antigen binding fragments may be separated from the Fc fragments by affinity chromatography, for example, using immobilized protein A or protein G, or immobilized DSP-11 polypeptide, or a suitable variant or fragment thereof. Those having ordinary skill in the art can routinely and without undue experimentation determine what is a suitable variant or fragment based on characterization of affinity purified antibodies obtained, for example, using immunodetection methods as provided herein. An alternative method to generate Fab fragments includes mild reduction of F(ab')$_2$ fragments followed by alkylation. See, e.g., Weir, *Handbook of Experimental Immunology*, 1986, Blackwell Scientific, Boston.

According to certain embodiments, non-human, human, or humanized heavy chain and light chain variable regions of any of the above described Ig molecules may be constructed as single chain Fv (sFv) polypeptide fragments (single chain antibodies). See, e.g., Bird et al., 1988 *Science* 242:423–426; Huston et al., 1988 *Proc. Natl. Acad. Sci. USA* 85:5879–5883. Multi-functional sFv fusion proteins may be generated by linking a polynucleotide sequence encoding an sFv polypeptide in-frame with at least one polynucleotide sequence encoding any of a variety of known effector proteins. These methods are known in the art, and are disclosed, for example, in EP-B1–0318554, U.S. Pat. No. 5,132,405, U.S. Pat. No. 5,091,513, and U.S. Pat. No. 5,476,786. By way of example, effector proteins may include immunoglobulin constant region sequences. See, e.g., Hollenbaugh et al., 1995 *J. Immunol. Methods* 188:1–7. Other examples of effector proteins are enzymes. As a non-limiting example, such an enzyme may provide a biological activity for therapeutic purposes (see, e.g., Siemers et al., 1997 *Bioconjug. Chem.* 8:510–19), or may provide a detectable activity, such as horseradish peroxidase-catalyzed conversion of any of a number of well-known substrates into a detectable product, for diagnostic uses. Still other examples of sFv fusion proteins include Ig-toxin fusions, or immunotoxins, wherein the sFv polypeptide is linked to a toxin. Those having ordinary skill in the art will appreciate that a wide variety of polypeptide sequences have been identified that, under appropriate conditions, are toxic to cells. As used herein, a toxin polypeptide for inclusion in an immunoglobulin-toxin fusion protein may be any polypeptide capable of being introduced to a cell in a manner that compromises cell survival, for example, by directly interfering with a vital function or by inducing apoptosis. Toxins thus may include, for example, ribosome-inactivating proteins, such as *Pseudomonas aeruginosa* exotoxin A, plant gelonin, bryodin from *Bryonia dioica,* or the like. See, e.g., Thrush et al., 1996 *Annu. Rev. Immunol.* 14:49–71; Frankel et al., 1996 *Cancer Res.* 56:926–32. Numerous other toxins, including chemotherapeutic agents, anti-mitotic agents, antibiotics, inducers of apoptosis (or "apoptogens", see, e.g., Green and Reed, 1998, *Science* 281:1309–1312), or the like, are known to those familiar with the art, and the examples provided herein are intended to be illustrative without limiting the scope and spirit of the invention.

The sFv may, in certain embodiments, be fused to peptide or polypeptide domains that permit detection of specific binding between the fusion protein and antigen (e.g., a DSP-11). For example, the fusion polypeptide domain may be an affinity tag polypeptide. Binding of the sFv fusion protein to a binding partner (e.g., a DSP-11) may therefore be detected using an affinity polypeptide or peptide tag, such as an avidin, streptavidin or a His (e.g., polyhistidine) tag, by any of a variety of techniques with which those skilled in the art will be familiar. Detection techniques may also include, for example, binding of an avidin or streptavidin fusion protein to biotin or to a biotin mimetic sequence (see, e.g., Luo et al., 1998 *J. Biotechnol.* 65:225 and references cited therein), direct covalent modification of a fusion protein with a detectable moiety (e.g., a labeling moiety), non-covalent binding of the fusion protein to a specific labeled reporter molecule, enzymatic modification of a detectable substrate by a fusion protein that includes a portion having enzyme activity, or immobilization (covalent or non-covalent) of the fusion protein on a solid-phase support.

The sFv fusion protein of the present invention, comprising a DSP-11-specific immunoglobulin-derived polypeptide fused to another polypeptide such as an effector peptide having desirable affinity properties, may therefore include, for example, a fusion protein wherein the effector peptide is an enzyme such as glutathione-S-transferase. As another example, sFv fusion proteins may also comprise a DSP-11-specific Ig polypeptide fused to a *Staphylococcus aureus* protein A polypeptide; protein A encoding nucleic acids and their use in constructing fusion proteins having affinity for immunoglobulin constant regions are disclosed generally, for example, in U.S. Pat. No. 5,100,788. Other useful affinity polypeptides for construction of sFv fusion proteins may include streptavidin fusion proteins, as disclosed, for example, in WO 89/03422; U.S. Pat. No. 5,489,528; U.S. Pat. No. 5,672,691; WO 93/24631; U.S. Pat. No. 5,168,049; U.S. Pat. No. 5,272,254 and elsewhere, and avidin fusion proteins (see, e.g., EP 511,747). As provided herein, sFv polypeptide sequences may be fused to fusion polypeptide sequences, including effector protein sequences, that may include full length fusion polypeptides and that may alternatively contain variants or fragments thereof.

An additional method for selecting antibodies that specifically bind to a DSP-11 polypeptide or variant or fragment thereof is by phage display. See, e.g., Winter et al., 1994 *Annul. Rev. Immunol.* 12:433–55; Burton et al., 1994 *Adv. Immunol.* 57:191–280. Human or murine immunoglobulin variable region gene combinatorial libraries may be created in phage vectors that can be screened to select Ig fragments (Fab, Fv, sFv, or multimers thereof) that bind specifically to a DSP-11 polypeptide or variant or fragment thereof. See, e.g, U.S. Pat. No. 5,223,409; Huse et al., 1989 *Science* 246:1275–81; Kang et al., 1991 *Proc. Natl. Acad. Sci. USA* 88:4363–66; Hoogenboom et al., 1992 *J. Molec. Biol.* 227:381–388; Schlebusch et al., 1997 *Hybridoma* 16:47–52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein, for instance, gene III or gene VIII of M13, to create an M13 fusion protein. A fusion protein may be a fusion of the coat protein with the light chain variable region domain and/or with the heavy chain variable region domain.

According to certain embodiments, immunoglobulin Fab fragments may also be displayed on the phage particle, as follows. Polynucleotide sequences encoding Ig constant region domains may be inserted into the phage genome in frame with a coat protein. The phage coat fusion protein may thus be fused to an Ig light chain or heavy chain fragment (Fd). For example, from a human Ig library, the polynucleotide sequence encoding the human kappa constant region may be inserted into a vector in frame with the sequence encoding at least one of the phage coat proteins. Additionally or alternatively, the polynucleotide sequence encoding the human IgG1 CH1 domain may be inserted in frame with the sequence encoding at least one other of the phage coat proteins. A plurality of polynucleotide sequences encoding variable region domains (e.g., derived from a DNA library) may then be inserted into the vector in frame with the constant region-coat protein fusions, for expression of Fab fragments fused to a bacteriophage coat protein.

Phage that display an Ig fragment (e.g., an Ig V-region or Fab) that binds to a DSP-11 polypeptide may be selected by mixing the phage library with DSP-11 or a variant or a fragment thereof, or by contacting the phage library with a DSP-11 polypeptide immobilized on a solid matrix under conditions and for a time sufficient to allow binding. Unbound phage are removed by a wash, which typically may be a buffer containing salt (e.g., NaCl) at a low concentration, preferably with less than 100 mM NaCl, more preferably with less than 50 mM NaCl, most preferably with less than 10 mM NaCl, or, alternatively, a buffer containing no salt. Specifically bound phage are then eluted with an NaCl-containing buffer, for example, by increasing the salt concentration in a step-wise manner. Typically, phage that bind the DSP-11 with higher affinity will require higher salt concentrations to be released. Eluted phage may be propagated in an appropriate bacterial host, and generally, successive rounds of DSP-11 binding and elution can be repeated to increase the yield of phage expressing DSP-11 specific immunoglobulin. Combinatorial phage libraries may also be used for humanization of non-human variable regions. See, e.g., Rosok et al., 1996 *J. Biol. Chem.* 271:22611–18; Rader et al., 1998 *Proc. Natl. Acad. Sci. USA* 95:8910–15. The DNA sequence of the inserted immunoglobulin gene in the phage so selected may be determined by standard techniques. See, Sambrook et al., 1989 *Molecular Cloning: A Laboratory Manual,* Cold Spring Harbor Press. The affinity selected Ig-encoding sequence may then be cloned into another suitable vector for expression of the Ig fragment or, optionally, may be cloned into a vector containing Ig constant regions, for expression of whole immunoglobulin chains.

Phage display techniques may also be used to select polypeptides, peptides or single chain antibodies that bind to DSP-11. For examples of suitable vectors having multicloning sites into which candidate nucleic acid molecules (e.g., DNA) encoding such peptides or antibodies may be inserted, see, e.g., McLafferty et al., *Gene* 128:29–36, 1993; Scott et al., 1990 *Science* 249:386–390; Smith et al., 1993 *Methods Enzymol.* 217:228–257; Fisch et al., 1996, *Proc. Natl. Acad. Sci. USA* 93:7761–66. The inserted DNA molecules may comprise randomly generated sequences, or may encode variants of a known peptide or polypeptide domain that specifically binds to a DSP-11 polypeptide, or variant or fragment thereof, as provided herein. Generally, the nucleic acid insert encodes a peptide of up to 60 amino acids, more preferably a peptide of 3 to 35 amino acids, and still more preferably a peptide of 6 to 20 amino acids. The peptide encoded by the inserted sequence is displayed on the surface of the bacteriophage. Phage expressing a binding domain for a DSP-11 polypeptide may be selected on the basis of specific binding to an immobilized DSP-11 polypeptide as described above. As provided herein, well-known recombinant genetic techniques may be used to construct fusion proteins containing the fragment thereof. For example, a polypeptide may be generated that comprises a tandem array of two or more similar or dissimilar affinity selected DSP-11 binding peptide domains, in order to maximize binding affinity for DSP-11 of the resulting product.

In certain other embodiments, the invention contemplates DSP-11 specific antibodies that are multimeric antibody fragments. Useful methodologies are described generally, for example in Hayden et al. 1997, *Curr Opin. Immunol.* 9:201–12; Coloma et al., 1997 *Nat. Biotechnol.* 15:159–63). For example, multimeric antibody fragments may be created by phage techniques to form miniantibodies (U.S. Pat. No. 5,910,573) or diabodies (Holliger et al., 1997, *Cancer Immunol. Immunother.* 45:128–130). Multimeric fragments may be generated that are multimers of a DSP-11-specific Fv, or that are bispecific antibodies comprising a DSP-11-specific Fv noncovalently associated with a second Fv having a different antigen specificity. See, e.g., Koelemij et al., 1999 *J. Immunother.* 22:514–24. As another example, a multimeric antibody may comprise a bispecific antibody having two single chain antibodies or Fab fragments. According to certain related embodiments, a first Ig fragment may be specific for a first antigenic determinant on a DSP-11 polypeptide (or variant or fragment thereof), while a second Ig fragment may be specific for a second antigenic determinant of the DSP-11 polypeptide. Alternatively, in certain other related embodiments, a first immunoglobulin fragment may be specific for an antigenic determinant on a DSP-11 polypeptide or variant or fragment thereof, and a second immunoglobulin fragment may be specific for an antigenic determinant on a second, distinct (i.e., non-DSP-11) molecule. Also contemplated are bispecific antibodies that specifically bind DSP-11, wherein at least one antigen-binding domain is present as a fusion protein.

Introducing amino acid mutations into DSP-11-binding immunoglobulin molecules may be useful to increase the specificity or affinity for DSP-11, or to alter an effector function. Immunoglobulins with higher affinity for DSP-11 may be generated by site-directed mutagenesis of particular residues. Computer assisted three-dimensional molecular modeling may be employed to identify the amino acid residues to be changed, in order to improve affinity for the DSP-11 polypeptide. See, e.g., Mountain et al., 1992, *Biotechnol. Genet. Eng. Rev.* 10: 1–142. Alternatively, combinatorial libraries of CDRs may be generated in M13 phage and screened for immunoglobulin fragments with improved affinity. See, e.g., Glaser et al., 1992, *J. Immunol.* 149:3903–3913; Barbas et al., 1994 *Proc. Natl. Acad. Sci. USA* 91:3809–13; U.S. Pat. No. 5,792,456).

Effector functions may also be altered by site-directed mutagenesis. See, e.g., Duncan et al., 1988 *Nature* 332:563–64; Morgan et al., 1995 *Immunology* 86:319–24; Eghtedarzedeh-Kondri et al., 1997 *Biotechniques* 23:830–34. For example, mutation of the glycosylation site on the Fc portion of the immunoglobulin may alter the ability of the immunoglobulin to fix complement. See, e.g., Wright et al., 1997 *Trends Biotechnol.* 15:26–32. Other mutations in the constant region domains may alter the ability of the immunoglobulin to fix complement, or to effect antibody-dependent cellular cytotoxicity. See, e.g., Duncan et al., 1988 *Nature* 332:563–64; Morgan et al., 1995 *Immunology* 86:319–24; Sensel et al., 1997 *Mol. Immunol.* 34:1019–29.

The nucleic acid molecules encoding an antibody or fragment thereof that specifically binds DSP-11, as described herein, may be propagated and expressed according to any of a variety of well-known procedures for nucleic acid excision, ligation, transformation and transfection. Thus, in certain embodiments expression of an antibody fragment may be preferred in a prokaryotic host, such as *Escherichia coli* (see, e.g., Pluckthun et al., 1989 *Methods Enzymol.* 178:497–515). In certain other embodiments, expression of the antibody or a fragment thereof may be preferred in a eukaryotic host cell, including yeast (e.g.,

*Saccharomyces cerevisiae, Schizosaccharomyces pombe,* and *Pichia pastoris*), animal cells (including mammalian cells) or plant cells. Examples of suitable animal cells include, but are not limited to, myeloma, COS, CHO, or hybridoma cells. Examples of plant cells include tobacco, corn, soybean, and rice cells. By methods known to those having ordinary skill in the art and based on the present disclosure, a nucleic acid vector may be designed for expressing foreign sequences in a particular host system, and then polynucleotide sequences encoding the DSP-11 binding antibody (or fragment thereof) may be inserted. The regulatory elements will vary according to the particular host.

A DSP-11-binding immunoglobulin (or fragment thereof) as described herein may contain a detectable moiety or label such as an enzyme, cytotoxic agent or other reporter molecule, including a dye, radionuclide, luminescent group, fluorescent group, or biotin, or the like. The DSP-11-specific immunoglobulin or fragment thereof may be radiolabeled for diagnostic or therapeutic applications. Techniques for radiolabeling of antibodies are known in the art. See, e.g., Adams 1998 *In Vivo* 12:11–21; Hiltunen 1993 *Acta Oncol.* 32:831–9. Therapeutic applications are described in greater detail below and may include use of the DSP-11-binding antibody (or fragment thereof) in conjunction with other therapeutic agents. The antibody or fragment may also be conjugated to a cytotoxic agent as known in the art and provided herein, for example, a toxin, such as a ribosome-inactivating protein, a chemotherapeutic agent, an anti-mitotic agent, an antibiotic or the like.

The invention also contemplates the generation of anti-idiotype antibodies that recognize an antibody (or antigen-binding fragment thereof) that specifically binds to DSP-11 as provided herein, or a variant or fragment thereof. Anti-idiotype antibodies may be generated as polyclonal antibodies or as monoclonal antibodies by the methods described herein, using an anti-DSP-11 antibody (or antigen-binding fragment thereof) as immunogen. Anti-idiotype antibodies or fragments thereof may also be generated by any of the recombinant genetic engineering methods described above, or by phage display selection. An anti-idiotype antibody may react with the antigen binding site of the anti-DSP-11 antibody such that binding of the anti-DSP-11 antibody to a DSP-11 polypeptide is competitively inhibited. Alternatively, an anti-idiotype antibody as provided herein may not competitively inhibit binding of an anti-DSP-11 antibody to a DSP-11 polypeptide.

As provided herein and according to methodologies well known in the art, polyclonal and monoclonal antibodies may be used for the affinity isolation of DSP-11 polypeptides. See, e.g., Hermanson et al., *Immobilized Affinity Ligand Techniques,* Academic Press, Inc. New York, 1992. Briefly, an antibody (or antigen-binding fragment thereof) may be immobilized on a solid support material, which is then contacted with a sample comprising the polypeptide of interest (e.g., a DSP-11). Following separation from the remainder of the sample, the polypeptide is then released from the immobilized antibody.

METHODS FOR DETECTING DSP-11 EXPRESSION

Certain aspects of the present invention provide methods that employ antibodies raised against DSP-11, or hybridizing polynucleotides, for diagnostic and assay purposes. Certain assays involve using an antibody or other agent to detect the presence or absence of DSP-11, or proteolytic fragments thereof. Alternatively, nucleic acid encoding DSP-11 may be detected, using standard hybridization and/or PCR techniques. Suitable probes and primers may be designed by those having ordinary skill in the art based on the DSP-11 cDNA sequence provided herein. Assays may generally be performed using any of a variety of samples obtained from a biological source, such as eukaryotic cells, bacteria, viruses, extracts prepared from such organisms and fluids found within living organisms. Biological samples that may be obtained from a patient include blood samples, biopsy specimens, tissue explants, organ cultures and other tissue or cell preparations. A patient or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines and the like. In certain preferred embodiments the patient or biological source is a human, and in certain preferred embodiments the biological source is a non-human animal that is a mammal, for example, a rodent (e.g., mouse, rat, hamster, etc.), an ungulate (e.g., bovine) or a non-human primate. In certain other preferred embodiments of the invention, a patient may be suspected of having or being at risk for having a disease associated with altered cellular signal transduction, or may be known to be free of a risk for or presence of such as disease.

To detect DSP-11 protein, the reagent is typically an antibody, which may be prepared as described below. There are a variety of assay formats known to those having ordinary skill in the art for using an antibody to detect a polypeptide in a sample. See, e.g., Harlow and Lane, *Antibodies: A Laboratory Manual,* Cold Spring Harbor Laboratory, 1988. For example, the assay may be performed in a Western blot format, wherein a protein preparation from the biological sample is resolved by gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the target DSP-11 and remove it from the remainder of the sample. The bound DSP-11 may then be detected using a second antibody or reagent that contains a reporter group. Alternatively, a competitive assay may be utilized, in which a DSP-11 polypeptide is labeled with a reporter group and allowed to bind to the immobilized antibody after incubation of the antibody with the sample. The extent to which components of the sample inhibit the binding of the labeled polypeptide to the antibody is indicative of the reactivity of the sample with the immobilized antibody, and as a result, indicative of the level of DSP-11 in the sample.

The solid support may be any material known to those having ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain embodiments, the assay for detection of DSP-11 in a sample is a two-antibody sandwich assay. This assay may be performed by first contacting an antibody that has been immobilized on a solid support, commonly the well of a microtiter plate, with the biological sample, such that DSP-11 within the sample is allowed to bind to the immobilized antibody (a 30 minute incubation time at room temperature is generally sufficient). Unbound sample is then removed from the immobilized DSP-11/antibody complexes and a second antibody (containing a reporter group such as an enzyme, dye, radionuclide, luminescent group, fluorescent group or biotin) capable of binding to a different site on the DSP-11 is added. The amount of second antibody that remains bound to the solid support is then determined using a method appropriate for the specific reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of DSP-11 in a sample, using well known techniques.

In a related aspect of the present invention, kits for detecting DSP-11 and DSP-11 phosphatase activity are provided. Such kits may be designed for detecting the level of DSP-11 or nucleic acid encoding DSP-11, or may detect phosphatase activity of DSP-11 in a direct phosphatase assay or a coupled phosphatase assay. In general, the kits of the present invention comprise one or more containers enclosing elements, such as reagents or buffers, to be used in the assay.

A kit for detecting the level of DSP-11, or nucleic acid encoding DSP-11, typically contains a reagent that binds to the DSP-11 protein, DNA or RNA. To detect nucleic acid encoding DSP-11, the reagent may be a nucleic acid probe or a PCR primer. To detect DSP-11 protein, the reagent is typically an antibody. Such kits also contain a reporter group suitable for direct or indirect detection of the reagent (i.e., the reporter group may be covalently bound to the reagent or may be bound to a second molecule, such as Protein A, Protein G, immunoglobulin or lectin, which is itself capable of binding to the reagent). Suitable reporter groups include, but are not limited to, enzymes (e.g., horseradish peroxidase), substrates, cofactors, inhibitors, dyes, radionuclides, luminescent groups, fluorescent groups and biotin. Such reporter groups may be used to directly or indirectly detect binding of the reagent to a sample component using standard methods known to those having ordinary skill in the art.

Kits for detecting DSP-11 activity typically comprise a DSP-11 substrate in combination with a suitable buffer. DSP-11 activity may be specifically detected by performing an immunoprecipitation step with a DSP-11-specific antibody prior to performing a phosphatase assay as described above. Other reagents for use in detecting dephosphorylation of substrate may also be provided.

Within certain diagnostic assays, a proliferative disorder may be detected in a patient or any other biological source organism as provided herein based on the presence of an altered DSP-11 or an altered level of DSP-11 expression. For example, an antibody may distinguish between a wild-type DSP-11 and an altered DSP-11 having a variation in amino acid sequence. Such a variation may be indicative of the presence of a proliferative disorder, or of susceptibility to such a disorder. Hybridization and amplification techniques may be similarly used to detect modified DSP-11 sequences.

METHODS FOR IDENTIFYING MODULATORS OF DSP-11 ACTIVITY

In one aspect of the present invention, DSP-11 polypeptides may be used to identify agents that modulate DSP-11 activity. Such agents may inhibit or enhance signal transduction via a MAP-kinase cascade, leading to cell proliferation. An agent that modulates DSP-11 activity may alter expression and/or stability of DSP-11, DSP-11 protein activity and/or the ability of DSP-11 to dephosphorylate a substrate. Agents that may be screened within such assays include, but are not limited to, antibodies and antigen-binding fragments thereof, competing substrates or peptides that represent, for example, a catalytic site or a dual phosphorylation motif, antisense polynucleotides and ribozymes that interfere with transcription and/or translation of DSP-11 and other natural and synthetic molecules, for example small molecule inhibitors, that bind to and inactivate DSP-11.

Candidate agents for use in a method of screening for a modulator of DSP-11 according to the present invention may be provided as "libraries" or collections of compounds, compositions or molecules. Such molecules typically include compounds known in the art as "small molecules" and having molecular weights less than $10^5$ daltons, preferably less than $10^4$ daltons and still more preferably less than $10^3$ daltons. For example, members of a library of test compounds can be administered to a plurality of samples, each containing at least one DSP-11 polypeptide as provided herein, and then assayed for their ability to enhance or inhibit DSP-11-mediated dephosphorylation of, or binding to, a substrate. Compounds so identified as capable of influencing DSP-11 function (e.g., phosphotyrosine and/or phosphoserine/threonine dephosphorylation) are valuable for therapeutic and/or diagnostic purposes, since they permit treatment and/or detection of diseases associated with DSP-11 activity. Such compounds are also valuable in research directed to molecular signaling mechanisms that involve DSP-11, and to refinements in the discovery and development of future DSP-11 compounds exhibiting greater specificity.

Candidate agents further may be provided as members of a combinatorial library, which preferably includes synthetic agents prepared according to a plurality of predetermined chemical reactions performed in a plurality of reaction vessels. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides (see e.g., PCT/US91/08694, PCT/US91/04666, which are hereby incorporated by reference in their entireties) or other compositions that may include small molecules as provided herein (see e.g., PCT/US94/08542, EP 0774464, U.S. Pat. No. 5,798,035, U.S. Pat. No. 5,789,172, U.S. Pat. No. 5,751,629, which are hereby incorporated by reference in their entireties). Those having ordinary skill in the art will appreciate that a diverse assortment of such libraries may be prepared according to established procedures, and tested using DSP-11 according to the present disclosure.

In certain embodiments, modulating agents may be identified by combining a candidate agent with a DSP-11 polypeptide or a polynucleotide encoding such a polypeptide, in vitro or in vivo, and evaluating the effect of the candidate agent on the DSP-11 phosphatase activity using, for example, a representative assay described herein. An increase or decrease in phosphatase activity can be measured by performing a representative assay provided herein in the presence and absence of a candidate agent.

Briefly, a candidate agent may be included in a mixture of active DSP-11 polypeptide and substrate (e.g., a phosphorylated MAP-kinase), with or without pre-incubation with one or more components of the mixture. In general, a suitable amount of antibody or other agent for use in such an assay ranges from about 0.01 µM to about 100 µM. The effect of the agent on DSP-11 activity may then be evaluated by quantifying the loss of phosphate from the substrate, and comparing the loss with that achieved using DSP-11 without the addition of a candidate agent. Alternatively, a coupled kinase assay may be used, in which DSP-11 activity is indirectly measured based on MAP-kinase activity.

Alternatively, a polynucleotide comprising a DSP-11 promoter operably linked to a DSP-11 coding region or reporter gene may be used to evaluate the effect of a test compound on DSP-11 transcription. Such assays may be performed in cells that express DSP-11 endogenously (e.g., human or other mammalian kidney or liver) or in cells transfected with an expression vector comprising a DSP-11 promoter linked to a reporter gene. The effect of a test compound may then be evaluated by assaying the effect on transcription of DSP-11 or the reporter using, for example, a Northern blot analysis or a suitable reporter activity assay.

DSP-11 activity may also be measured in whole cells transfected with a reporter gene whose expression is dependent upon the activation of an appropriate substrate. For example, appropriate cells (i.e., cells that express DSP-11) may be transfected with a substrate-dependent promoter linked to a reporter gene. In such a system, expression of the reporter gene (which may be readily detected using methods well known to those of ordinary skill in the art) depends upon activation of substrate. Dephosphorylation of substrate may be detected based on a decrease in reporter activity. Candidate modulating agents may be added to such a system, as described above, to evaluate their effect on DSP-11 activity.

The present invention further provides methods for identifying a molecule that interacts with, or binds to, DSP-11. Such a molecule generally associates with DSP-11 with an affinity constant ($K_a$) of at least $10^4$, preferably at least $10^5$, more preferably at least $10^6$, still more preferably at least $10^7$ and most preferably at least $10^8$. Affinity constants may be determined using well known techniques. Methods for identifying interacting molecules may be used, for example, as initial screens for modulating agents, or to identify factors that are involved in the in vivo DSP-11 activity. Techniques for substrate trapping, for example using of DSP-11 variants or substrate trapping mutants as described above, are also contemplated according to certain embodiments provided herein. In addition to standard binding assays, there are many other techniques that are well known for identifying interacting molecules, including yeast two-hybrid screens, phage display and affinity techniques. Such techniques may be performed using routine protocols, which are well known to those having ordinary skill in the art (see, e.g., Bartel et al., In *Cellular Interactions in Development: A Practical Approach,* D. A. Harley, ed., Oxford University Press (Oxford, UK), pp. 153–179, 1993). Within these and other techniques, candidate interacting proteins (e.g., putative DSP-11 substrates) may be phosphorylated prior to assaying for the presence of DSP-11-binding or interacting proteins.

Within other aspects, the present invention provides animal models in which an animal either does not express a functional DSP-11, or expresses an altered DSP-11. Such animals may be generated using standard homologous recombination strategies. Animal models generated in this manner may be used to study activities of DSP-11 polypeptides and modulating agents in vivo.

METHODS FOR DEPHOSPHORYLATING A SUBSTRATE

In another aspect of the present invention, a DSP-11 polypeptide may be used for dephosphorylating a substrate of DSP-11 as provided herein. In one embodiment, a substrate may be dephosphorylated in vitro by incubating a DSP-11 polypeptide with a substrate in a suitable buffer (e.g., Tris, pH 7.5, 1 mM EDTA, 1 mM dithiothreitol, 1 mg/mL bovine serum albumin) for 10 minutes at 30° C. Any compound that can be dephosphorylated by DSP-11, such as a MAP-kinase, may be used as a substrate. In general, the amounts of the reaction components may range from about 50 pg to about 50 ng of DSP-11 polypeptide and from about 10 ng to about 10 µg of substrate. Dephosphorylated substrate may then be purified, for example, by affinity techniques and/or gel electrophoresis. The extent of substrate dephosphorylation may generally be monitored by adding [$\gamma$-$^{32}$P]labeled substrate to a test aliquot, and evaluating the level of substrate dephosphorylation as described herein.

METHODS FOR MODULATING CELLULAR RESPONSES

Modulating agents may be used to modulate, modify or otherwise alter (e.g., alter increase or decrease) cellular responses such as cell proliferation, differentiation and survival, in a variety of contexts, both in vivo and in vitro. In general, to so modulate (e.g., increase or decrease in a statistically significant manner) such a response, a cell is contacted with an agent that modulates DSP-11 activity, under conditions and for a time sufficient to permit modulation of DSP-11 activity. Agents that modulate a cellular response may function in any of a variety of ways. For example, an agent may modulate a pattern of gene expression (i.e., may enhance or inhibit expression of a family of genes or genes that are expressed in a coordinated fashion). A variety of hybridization and amplification techniques are available for evaluating patterns of gene expression. Alternatively, or in addition, an agent may effect apoptosis or necrosis of the cell, and/or may modulate the functioning of the cell cycle within the cell. (See, e.g., Ashkenazi et al., 1998 *Science,* 281:1305; Thornberry et al., 1998 *Science* 281:1312; Evan et al., 1998 *Science* 281:1317; Adams et al., 1998 *Science* 281:1322; and references cited therein.)

Cells treated as described above may exhibit standard characteristics of cells having altered proliferation, differentiation or survival properties. In addition, such cells may (but need not) display alterations (e.g., statistically significant increases or decreases) in other detectable properties, such as contact inhibition of cell growth, anchorage independent growth or altered intercellular adhesion. Such properties may be readily detected using techniques wit hwhich those having ordinary skill in the art will be familiar.

THERAPEUTIC METHODS

One or more DSP-11 polypeptides, modulating agents (including any agent that specifically binds a DSP-11, such as an antibody or fragment thereof as provided herein) and/or polynucleotides encoding such polypeptides and/or modulating agents may also be used to modulate DSP-11 activity in a patient. As used herein, a "patient" may be any mammal, including a human, and may be afflicted with a condition associated with DSP-11 activity or may be free of detectable disease. Accordingly, the treatment may be of an existing disease or may be prophylactic. Conditions associated with DSP-11 activity include any disorder associated with cell proliferation, including Duchenne muscular dystrophy, cancer, graft-versus-host disease (GVHD), autoimmune diseases, allergy or other conditions in which immunosuppression may be involved, metabolic diseases, abnormal cell growth or proliferation and cell cycle abnormalities. Certain such disorders involve loss of normal MAP-kinase phosphatase activity, leading to uncontrolled cell growth. DSP-11 polypeptides, and polynucleotides encoding such polypeptides, can be used to ameliorate such disorders.

For administration to a patient, one or more polypeptides, polynucleotides and/or modulating agents are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Such compositions may be in the form of a solid, liquid or gas (aerosol). Alternatively, compositions of the present invention may be formulated as a lyophilizate or compounds may be encapsulated within liposomes using well known technology. Pharmaceutical compositions within the scope of the present invention may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable carrier known to those of ordinary skill in the art may be employed in the pharmaceutical compositions of the present invention. Carriers for therapeutic use are well known, and are described, for example, in *Remingtons Pharmaceutical Sciences,* Mack Publishing Co. (A. R. Gennaro ed. 1985). In general, the type of carrier is selected based on the mode of administration. Pharmaceutical compositions may be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The compositions described herein may be formulated for sustained release (i.e., a formulation such as a capsule or sponge that effects a slow release of compound following administration). Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

For pharmaceutical compositions comprising a polynucleotide encoding a DSP-11 polypeptide and/or modulating agent (such that the polypeptide and/or modulating agent is generated in situ), the polynucleotide may be present within any of a variety of delivery systems known to those of ordinary skill in the art, including nucleic acid, and bacterial, viral and mammalian expression systems. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

Within a pharmaceutical composition, a DSP-11 polypeptide, polynucleotide or modulating agent may be linked to any of a variety of compounds. For example, such an agent may be linked to a targeting moiety (e.g., a monoclonal or polyclonal antibody, a protein or a liposome) that facilitates the delivery of the agent to the target site. As used herein, a "targeting moiety" may be any substance (such as a compound or cell) that, when linked to an agent enhances the transport of the agent to a target cell or tissue, thereby increasing the local concentration of the agent. Targeting moieties include antibodies or fragments thereof, receptors, ligands and other molecules that bind to cells of, or in the vicinity of, the target tissue. An antibody targeting agent may be an intact (whole) molecule, a fragment thereof, or a functional equivalent thereof. Examples of antibody fragments are $F(ab')_2$, –Fab', Fab and F[v] fragments, which may be produced by conventional methods or by genetic or protein engineering. Linkage is generally covalent and may be achieved by, for example, direct condensation or other reactions, or by way of bi- or multi-functional linkers. Targeting moieties may be selected based on the cell(s) or tissue(s) toward which the agent is expected to exert a therapeutic benefit.

Pharmaceutical compositions may be administered in a manner appropriate to the disease to be treated (or prevented). An appropriate dosage and a suitable duration and frequency of administration will be determined by such factors as the condition of the patient, the type and severity of the patient's disease, the particular form of the active ingredient and the method of administration. In general, an appropriate dosage and treatment regimen provides the agent(s) in an amount sufficient to provide therapeutic and/or prophylactic benefit (e.g., an improved clinical outcome, such as more frequent complete or partial remissions, or longer disease-free and/or overall survival). For prophylactic use, a dose should be sufficient to prevent, delay the onset of or diminish the severity of a disease associated with cell proliferation.

Optimal dosages may generally be determined using experimental models and/or clinical trials. In general, the amount of polypeptide present in a dose, or produced in situ by DNA present in a dose, ranges from about 0.01 μg to about 100 μg per kg of host, typically from about 0.1 μg to about 10 μg. The use of the minimum dosage that is sufficient to provide effective therapy is usually preferred. Patients may generally be monitored for therapeutic or prophylactic effectiveness using assays suitable for the condition being treated or prevented, which will be familiar to those having ordinary skill in the art. Suitable dose sizes will vary with the size of the patient, but will typically range from about 10 mL to about 500 mL for 10–60 kg animal.

The following Examples are offered by way of illustration and not by way of limitation.

EXAMPLES

Example 1

CLONING AND SEQUENCING cDNA ENCODING DSP-11

This Example illustrates the cloning of a cDNA molecule encoding human DSP-11.

A conserved sequence motif defining a novel homology domain of dual-specificity phosphatases was identified as follows: Dual specificity phosphatases belong to the larger family of protein tyrosine phosphatases (PTPs) that share a conserved catalytic domain containing a cysteine residue situated N-terminal to a stretch of five variable amino acids followed by an arginine residue (Fauman et al., *Trends In Bioch. Sci.* 21:413–417, 1996). DSPs typically contain a PTP active site motif but lack sequence homology to PTPs in other regions (Jia, *Biochem. and Cell Biol.* 75:17–26, 1997). There is, however, no reported consensus sequence that is conserved among DSPs, nor is a consensus region apparent from examination of the known DSP sequences such as those referred to above. To derive a longer consensus DSP amino acid sequence motif that would be useful for the identification of new DSP family members, multiple known human dual-specificity phosphatases sequences were aligned and compared. From an alignment of eight amino acid sequences derived from eight particular human DSPs having MAP-kinase phosphatase activity (FIG. 3), a candidate conserved homology region was identified. This homology region consisted of a 24-amino acid peptide sequence, based on analysis of the DSP regions situated on either side of, and including, the PTP active site signature motif. Thus, a candidate peptide having the sequence:

NGRVLVHCQAGISRSGTNILAYLM SEQ ID NO:4 was used to search the Expressed Sequence Tag database (Nat. Center for Biol. Information, www.ncbi.nlm.nih.gov/dbEST). The search employed an algorithm (tblastn) capable of reverse translation of the candidate peptide with iterations allowing for genetic code degeneracy within default parameters. The search results identified the EST AA479435 as a candidate MAP-kinase phosphatase sequence. Additional tblastn searches with the EST AA479435 identified the following ESTs comprising candidate partial carboxyterminal DSP-11 coding sequences: AI1363485, AI309010, AI341528, AI302179, AA863013, AA341644; these searches also identified the uncharacterized (i.e., not an EST) partial cDNA fragment AF086553. The ESTs did not include a complete coding region of an expressed gene such as a gene encoding a DSP-11 having MAP-kinase phosphatase activity, or any region encoding a PTP active site, nor were the sense strand and open reading frame identified.

To obtain a full length coding region, human kidney cDNA (reverse transcribed from human kidney RNA) was screened in 5' and 3' RACE (rapid amplification of cDNA ends) reactions as described (Frohman et al., *Proc. Nat. Acad. Sci. USA* 85:8998, 1988; Ohara et al., *Proc. Nat. Acad. Sci. USA* 86:5673, 1989; Loh et al., *Science* 243:217, 1989) using 5'/3' RACE kits (Clontech, Palo Alto, Calif.; Life Technologies, Inc., Gaithersburg, Md.) according to the supplier's instructions. Sequence information immediately adjacent to the conserved sequence motif of EST AA479435 was used in the 5' and 3' RACE reactions with human kidney cDNA, using the following primers (SEQ ID NOS:5 to 7):

```
DSP11-GSP1:
5'-CGGGTCGTAGTCGTCGGATTTCAGCAA-3'      SEQ ID NO:5

DSP11-GSP2:
5'-CCTCTCCCCGTGCGTTGGCCTCGT-3'         SEQ ID NO:6

DSP11-SP5
5'-CGC ACG GGG AGA GGC TGT-3'          SEQ ID NO:7
```

Sequences of the resulting RACE 5' products indicated the presence of an open reading frame, but the deduced translated sequences lacked an initiating methionine. RACE 3' products generated with the DSP-11-SP5 primer (SEQ ID NO:7) and having an open reading frame included a stop codon, indicating that a DSP-11 coding region 3' terminus had been identified. To determine the DSP-11 coding region 5' terminus, the deduced sequence was used to search the EST database as described above and additional ESTs, AA101787 and AA159216, were identified that corresponded to the 5' RACE product derived sequence. To confirm the DSP-11 full-length coding sequence and to account for apparent minor sequence differences between these ESTs, the following primers for the full length DSP-11 protein were designed to establish the coding region for the DSP-11 amino terminus:

```
DSP11EX5':
5'-GAG GAA TAA TAA ATG ACC CGC TGT CCT GTG CCC TTT CCC AG-3'   SEQ ID NO:8

DSP11EX3':
5'-TTTCGTTCGCTGGTAGAACTGGAAGACTGCTTTC-3'                        SEQ ID NO:9
```

PCR amplification from kidney cDNA templates using the primer pair DSP11EX5' [SEQ ID NO:8] and DSP11-EX3' [SEQ ID NO:9] yielded an amplicon having the predicted sequence, including sequences encoding initiating methionine of DSP-11 plus two base pairs 5' to the ATG initiation codon at the 5' end, and a sequence encoding C-terminal lysine but, by design, lacking the stop codon at the 3' end. A cDNA (FIG. 1; SEQ ID NO:1) encoding a protein of 150 amino acids (FIG. 2; SEQ ID NO:2) was thus identified as DSP-11. This sequence has significant homology to other MAP-kinase phosphatases (FIG. 3). The identified cDNA contains the 450 base pair coding region, as well as associated 5' and 3' untranslated sequences (FIG. 1). The active site domain for DSP-11 was localized to the region encoded by nucleotides beginning at position 273 of SEQ ID NO:1.

Semiquantitative RT-PCR analyses were performed. These analyses showed detectable DSP-11 encoding mRNA in RNA sample from all human tissues analyzed, including brain, thymus, placenta, skeletal muscle, testes and adipose tissue, with apparently higher DSP-11 expression levels in kidney and liver.

Example 2

DSP-11 EXPRESSION IN HUMAN TISSUES

In this example, a DSP-11 encoding nucleic acid sequence is shown to hybridize to human polyA+ RNA from various tissue sources. Full length DSP-11 encoding cDNA (SEQ ID NO:1) was $^{32}$P-labeled by the random primer method as described in Ausubel et al. (1998 *Current Protocols in Molecular Biology*, Greene Publ. Assoc. Inc. & John Wiley & Sons, Inc., Boston, Mass.) for use as a nucleic acid hybridization probe. The probe was hybridized to blots containing human polyA+ RNA derived from multiple human tissues, normalized for the amount of detectable β-actin mRNA (FIG. 4, Cat. No. 7759-1; Clontech, Inc., Palo Alto, Calif.). Blots underwent prehybridization for 30 min at 68° C. in Express Hyb™ solution (Clontech), and then were hybridized with the labeled probe for 1 hour at 68° C. in Express Hyb™ solution. The blots were next washed for 40 min at room temperature in 2×SSC, 0.05% SDS, followed by a second wash for 40 min at 50° C. in 0.1×SSC, 0.1% SDS. Blots were then exposed to Hyperfilm MP™ autoradiographic film (Amersham Life Sciences, Arlington Hts, Ill.) overnight. Results are shown in FIG. 4, in which the human tissue sources for the RNAs were as follows: Lane 1, He, heart; lane 2, Br, brain; lane 3, Pl, placenta; lane 4, Lu, lung; lane 5, Li, liver; lane 6, SM, skeletal muscle; lane 7, Ki, kidney; lane 8, Pa, pancreas.

Example 3

IDENTIFICATION OF A MURINE DSP-11 VARIANT

This example describes identification of a murine DSP-11 variant, based on the DSP-11 sequence identified in Example 1. The full-length DSP-11 encoding polynucleotide sequence (SEQ ID NO:1) was submitted to the EST database (Nat. Center for Biol. Information, www.ncbi.nlm.nih.gov/dbEST) as a search sequence, using the Advanced BLAST algorithm and dbest options with the organism field restricted to *Mus musculus*, and the following two ESTs were obtained as best matches: AA023073 and AW258860.

Alignment of these two EST sequences with each other and with SEQ ID NO:1 showed high homology between a portion of AA023073 and the DSP-11 coding region of SEQ ID NO:1, while AW258860 exhibited high homology with a large portion of the DSP-11 coding sequence of SEQ ID NO:1 beginning with the N-terminal region, but lacked a polynucleotide region corresponding to the portion of SEQ ID NO:1 that encodes the DSP-11 C-terminal region. AA023073 and AW258860 displayed nucleotide sequence identity over the region corresponding to DSP-11 encoding nucleotides 1–316 of SEQ ID NO:1; 3' to this position the sequence of AA023073 could also be readily aligned with SEQ ID NO:1 but lacked a single base pair corresponding to DSP-11 encoding nucleotide position 353 of SEQ ID NO:1 and contained a C→G substitution in the coding strand at the nucleotide position corresponding to DSP-11 encoding nucleotide 438 of SEQ ID NO:1, thereby generating downstream a premature stop codon regardless of whether correction was made for the frameshift. Proceeding in the 3' direction from the position corresponding to DSP-11 encoding nucleotide 316 of SEQ ID NO:1, AW258860 diverged substantially.

Another EST identified in the database search described in this Example was W41278, the first nucleotide of wich could be aligned with the nucleotide at position 139 in the DSP-11 coding strand sequence o SEQ ID NO:1, to show essential identity with the portion of SEQ ID NO:1 that encodes the C-terminal region of DSP-11, moving in the 3' direction from position 139. W41278 lacked th C→G substitution that was present in the AA023073 coding strand at the nucleotide position corresponding to nt 438 of SEQ ID NO:1, as described above. From the sequence alignments of the ESTs, the complete coding sequence for the murine DSP-11 variant thus became apparent to yield the full length nucleotide sequence shown in FIG. 5 (SEQ ID NQ:12 which encode the murine DSP-11 variant polypeptide sequence shown in FIG. 6 (SEQ ID NO:13), wherein the mismatches identified in AA023073 that generate premature stop codons have been corrected according to the W41278 sequence.

To molecularly clone this murine DSP-11 variant, a polynucleotide containing the full length coding sequence is amplified from a murine placenta cDNA library using standard PCR conditions (annealing temperature of 72° C., 35 cycles) and the following primers:

```
mDSP-11-5':
5'-ATG GGC GTG CAA CCC CCC AAC TTC TCC-3'        (SEQ ID NO:10)

mDSP-11-3':
5'-TCA TTT TGT TCG CTG GTA GAA CTG GAA GAC GGC C-3'   (SEQ ID NO:11)
```

From the foregoing, it will be appreciated that, although specific embodiments of the invention have been described herein for the purpose of illustration, various modifications may be made without deviating from the spirit and scope of the invention. Accordingly, the present invention is not limited except as by the appended claims.

What is claimed is:

1. An isolated polypeptide comprising the sequence of DSP-11 recited in SEQ ID NO:2.

2. A DSP-11 substrate trapping mutant polypeptide that differs from the sequence recited in SEQ ID NO: 2 by a substitution at position 65 or position 95 of SEQ ID NO: 2, such that the polypeptide binds to a substrate with an affinity that is no substantially diminished relative to DSP-11, and such that the ability of the polypeptide to dephosphorylate a substrate is reduced relative to DSP-11.

3. An isolated polypeptide that is encoded by a polynucleotide which encodes a polypeptide capable of dephosphorylating an activated MAP-kinase, said polynucleotide comprising a seq ence at least 80% identical to a polynucleotide that encodes a polypeptide comprising an amin acid sequence set forth in SEQ ID NO:2.

4. An isolated polypeptide that is encoded by a polynucleotide which encodes a polypeptide capable of dephosphorylating an activated MAP-kinase, said polynucleotide comprising a seqence at least 90% identical to a polynucleotide that encodes a polypeptide comprising an amin acid sequence set forth in SEQ ID NO:2.

5. An isolated polypeptide that is encoded by a polynucleotide wherin the polypeptide capable of dephosphorylating an activated MAP-kinase, said polypeptide comprising an amino acid sequence of SEQ ID NO:2, wherein an aspartic acid is located at position 65 and the peptide s uence VGVHCALGFGRTGTMLACYLV (SEQ ID NO:3) is located at positions 91 through 111 of SEQ ID NO:2, wherein said polynucleotide comprises a sequence at least 80% identical o a polynucleotide that encodes a polypeptide comprising the amino acid sequence of SEQ ID NO:2.

* * * * *

UNITED STATES PATENT AND TRADEMARK OFFICE
CERTIFICATE OF CORRECTION

PATENT NO. : 7,029,898 B2 Page 1 of 1
APPLICATION NO. : 10/655073
DATED : April 18, 2006
INVENTOR(S) : Ralf M. Luche et al.

It is certified that error appears in the above-identified patent and that said Letters Patent is hereby corrected as shown below:

Column 47
Line 62, "no substantially" should read as --not substantially--.

Column 48
Line 55, "seq ence" should read as --sequence--.
Line 56, "amin" should read as --amino--.
Line 62, "seqence" should read as --sequence--.
Line 63, "amin" should read as --amino--.
Line 66, "wherin" should read as --wherein--.
Line 66, "polypeptide capable" should read as --polypeptide is capable--.

Column 49
Line 2, "s uence" should read as --sequence--.

Column 50
Line 1, "identical o a polynucleotide" should read as --identical to a polynucleotide--.

Signed and Sealed this

Nineteenth Day of September, 2006

JON W. DUDAS
*Director of the United States Patent and Trademark Office*